(12) United States Patent
Stewart et al.

(10) Patent No.: US 10,943,279 B2
(45) Date of Patent: Mar. 9, 2021

(54) SYSTEMS, METHODS AND APPARATUS FOR PRODUCING CUSTOMIZED TOPICAL AGENTS

(71) Applicant: Shiseido Company, Limited, Tokyo (JP)

(72) Inventors: Joel Stewart, Calabasas, CA (US); Leslie Y. Harvill, Half Moon Bay, CA (US); Rajesh Subramanian, San Jose, CA (US); David Espinoza, Downey, CA (US)

(73) Assignee: Shiseido Company, Limited, Tokyo (JP)

( * ) Notice: Subject to any disclaimer, the term of this patent is extended or adjusted under 35 U.S.C. 154(b) by 206 days.

(21) Appl. No.: 15/855,064

(22) Filed: Dec. 27, 2017

(65) Prior Publication Data
US 2018/0189853 A1    Jul. 5, 2018

Related U.S. Application Data

(63) Continuation of application No. PCT/US2017/064566, filed on Dec. 4, 2017.
(Continued)

(51) Int. Cl.
*G06Q 30/06* (2012.01)
*B01F 13/10* (2006.01)
(Continued)

(52) U.S. Cl.
CPC ..... *G06Q 30/0621* (2013.01); *B01F 13/1066* (2013.01); *B01F 13/1069* (2013.01);
(Continued)

(58) Field of Classification Search
CPC .. B65D 83/28; B01F 13/1055; G06Q 30/0621
(Continued)

(56) References Cited

U.S. PATENT DOCUMENTS 4,871,262 A * 10/1989 Krauss ............... B01F 13/1055
366/160.3
5,163,909 A    11/1992 Stewart
(Continued)

OTHER PUBLICATIONS

International Search Report and Written Opinion in Counterpart PCT/US2017/064566 (14 pages).

*Primary Examiner* — David L Sorkin
(74) *Attorney, Agent, or Firm* — Calderone Bullock LLC

(57) ABSTRACT

A method and a system are described herein for preparing a custom cosmetic formulation. The system includes a controller in electronic communication with an order management system, wherein the order management system stores user-specific data including data related to a custom cosmetic formulation and components thereof, a plurality of valves for receiving pressurized fluid, the plurality of valves in electronic communication with the controller; a plurality of dispensers, each having a valve for metering fluid in predetermined quantities, and each having a dispensing head having a nozzle, each nozzle comprising a nozzle tip on a distal end thereof, wherein the nozzle tips are arranged so as to dispense a fluid into an inlet of a product receptacle, the dispensers in electronic communication with a data port; a measuring device in electronic communication with the controller, the measuring device capable of capturing data related to dispensed fluids from each of the plurality of dispensers and transmitting the data to the controller; a barcode scanner for reading order-specific instructions; a user interface for operator communication with the order management system and with the controller; a plurality of fluid conduits for introducing fluid to the dispensers; a fluid delivery apparatus for delivery of components of a custom cosmetic component to the dispensers; and a pressure source for pressurizing fluid in the fluid delivery apparatus for
(Continued)

delivery of fluid from the fluid delivery apparatus to the plurality of dispensers.

35 Claims, 16 Drawing Sheets

Related U.S. Application Data

(60) Provisional application No. 62/429,216, filed on Dec. 2, 2016.

(51) Int. Cl.
  *G07F 13/06* (2006.01)
  *B65D 83/28* (2006.01)
  *B65D 83/54* (2006.01)
  *G06Q 10/08* (2012.01)
  *A61Q 17/00* (2006.01)

(52) U.S. Cl.
  CPC .......... *B65D 83/28* (2013.01); *B65D 83/54* (2013.01); *G06Q 10/087* (2013.01); *G07F 13/06* (2013.01); *A61K 2800/80* (2013.01); *A61Q 17/00* (2013.01)

(58) Field of Classification Search
  USPC .................................................. 222/77, 135
  See application file for complete search history.

(56) References Cited

U.S. PATENT DOCUMENTS

| | | | |
|---|---|---|---|
| 5,169,909 A | 12/1992 | Okawa | |
| 5,622,692 A | 4/1997 | Rigg et al. | |
| 5,903,465 A | 5/1999 | Brown | |
| 6,177,093 B1 | 1/2001 | Lombardi et al. | |
| 6,516,245 B1* | 2/2003 | Dirksing | A45D 40/00 700/233 |
| 6,622,064 B2* | 9/2003 | Bartholomew | A45D 29/00 222/144 |
| 6,935,386 B2* | 8/2005 | Miller | B01F 13/1055 141/104 |
| 7,437,344 B2 | 10/2008 | Peyrelevade | |
| 8,564,778 B1 | 10/2013 | Igarashi | |
| 8,593,634 B1 | 11/2013 | Igarashi | |
| 8,830,468 B2 | 9/2014 | Igarashi | |
| 8,856,160 B2 | 10/2014 | Beaver et al. | |
| 8,933,994 B2 | 1/2015 | Gross et al. | |
| 9,007,588 B1 | 4/2015 | Igrashi | |
| 9,122,918 B2 | 9/2015 | Howell et al. | |
| 9,122,919 B2 | 9/2015 | Howell et al. | |
| 9,427,187 B2 | 8/2016 | Gilbert | |
| 9,442,494 B2 | 9/2016 | Igarashi | |
| 9,449,412 B1 | 9/2016 | Rogers et al. | |
| 10,321,748 B2 | 6/2019 | Howell et al. | |
| 2003/0069667 A1 | 4/2003 | Dirksing et al. | |
| 2003/0215471 A1 | 11/2003 | Wilmott et al. | |
| 2008/0202945 A1 | 8/2008 | Ackermann | |
| 2008/0311061 A1 | 12/2008 | Heuer | |
| 2010/0245823 A1 | 9/2010 | Chhibber et al. | |
| 2011/0211047 A1 | 9/2011 | Chhibber et al. | |
| 2012/0216911 A1 | 8/2012 | Bartholomew et al. | |
| 2012/0229828 A1 | 9/2012 | Gill | |
| 2013/0076932 A1 | 3/2013 | Chhibber et al. | |
| 2014/0081463 A1 | 3/2014 | Igarashi | |
| 2014/0267664 A1* | 9/2014 | Gross | A61B 5/441 348/77 |
| 2014/0267665 A1* | 9/2014 | Howell | G06K 9/00221 348/77 |
| 2014/0267783 A1* | 9/2014 | Howell | G06Q 50/22 348/187 |
| 2014/0316723 A1 | 10/2014 | Rogers et al. | |
| 2015/0107678 A1 | 4/2015 | Igarashi | |
| 2016/0023175 A1 | 1/2016 | Herschap | |
| 2016/0107133 A1 | 4/2016 | Sugino et al. | |

* cited by examiner

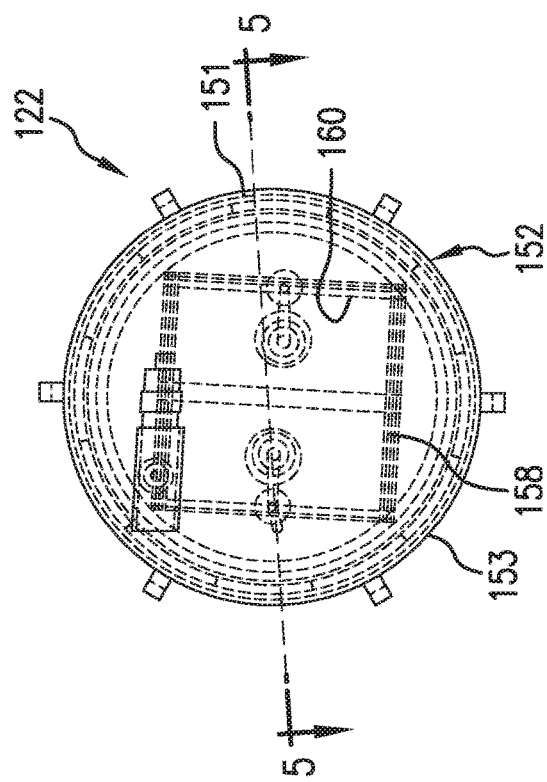
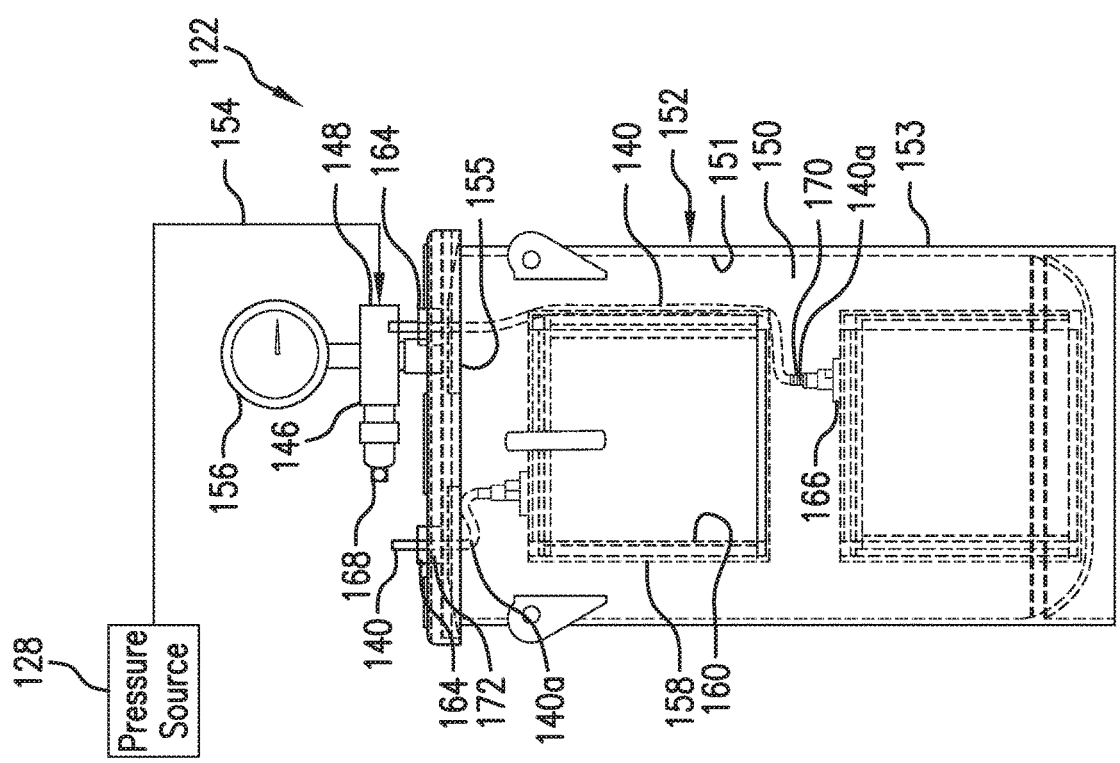

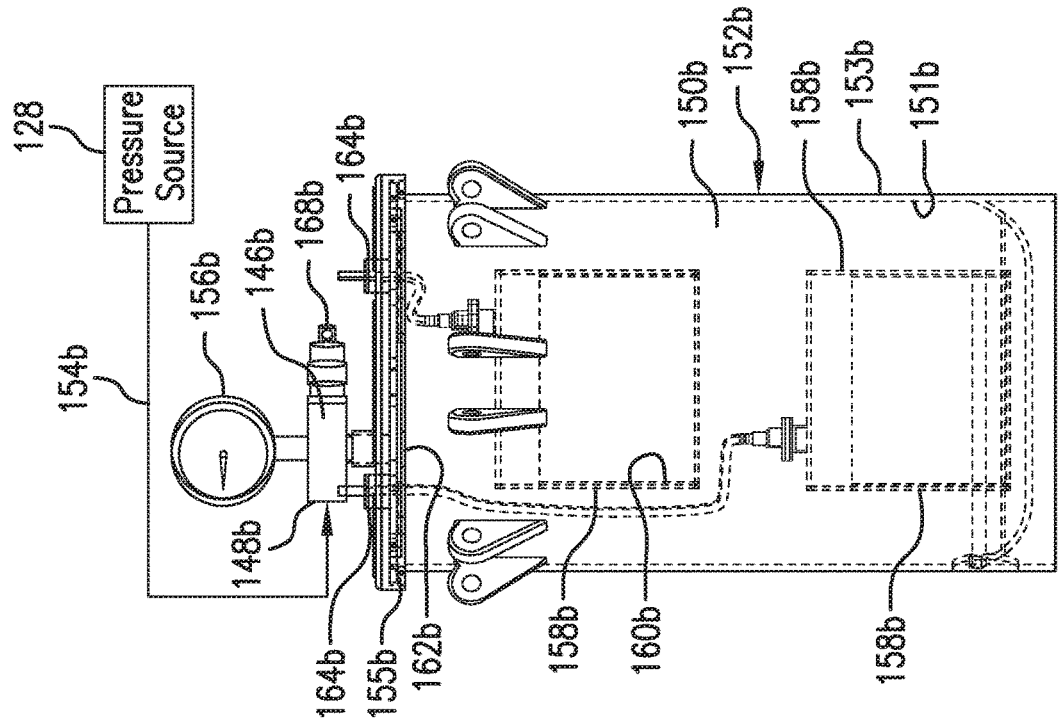
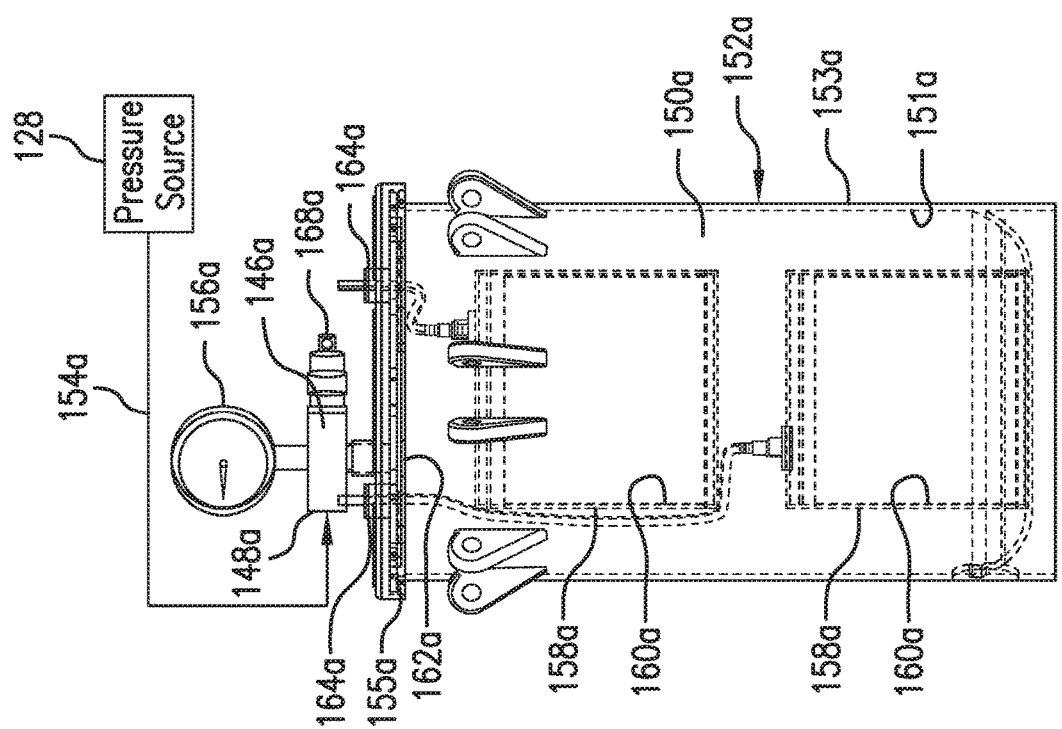

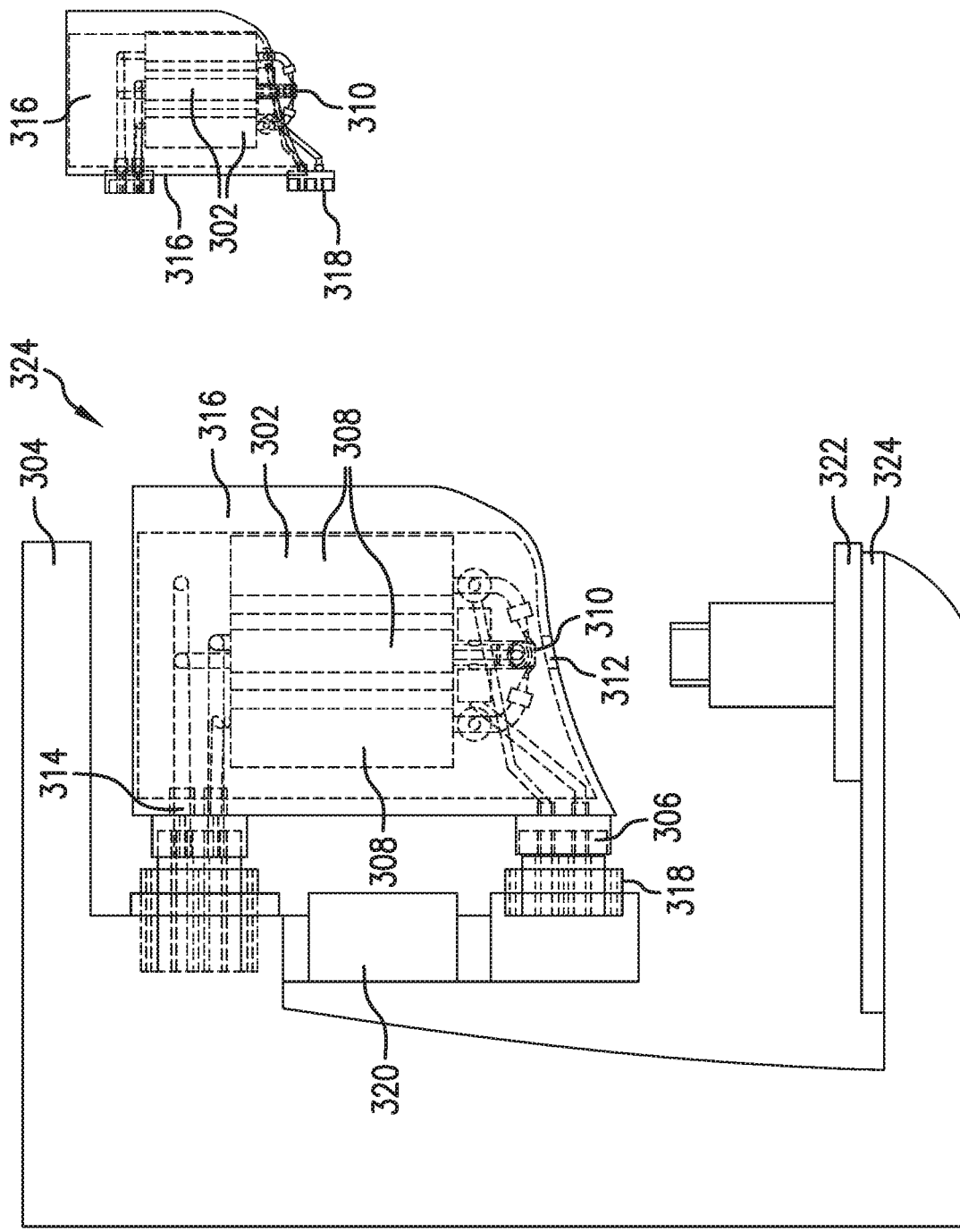

SYSTEMS, METHODS AND APPARATUS FOR PRODUCING CUSTOMIZED TOPICAL AGENTS

CROSS-REFERENCE TO RELATED APPLICATIONS

This application is a continuation of pending International Patent Application No. PCT/US2017/064566, filed Dec. 4, 2017 and entitled "Systems and Methods for Producing Customized Topical Agents" which application claims the benefit under 35 U.S.C. § 119(e) to U.S. Provisional Patent Application No. 62/429,216, filed Dec. 2, 2016, entitled "Systems and Methods for Producing Customized Topical Agents," the entire disclosure disclosures of which is are incorporated herein by reference.

BACKGROUND OF THE INVENTION

Field of the Invention

The present invention relates to designing a primary set of formulations for producing a cosmetic agent and methods, systems and an apparatus for combining such agents to produce a custom cosmetic.

Description of Related Art

Aesthetic and protective cosmetic topical agents in the form of applied creams or lotions are widely used to protect against UV radiation, provide moisture barriers, mask blemishes and skin discoloration, reduce or prevent irritation, and provide other healthful and aesthetic benefits. In the best of all possible worlds, these protective topical agents would be specified by a team of experts for a particular individual with specific needs, and for a specific environment or use. The topical agent would then be formulated in a timely manner and delivered to the individual. Unfortunately, logistics and cost have to date limited the practicality of providing such a specific, optimized product to a given user.

Currently, there are several approaches to provide cosmetic topical agents that match a particular need. These agents may be compounded based on a specification from a dermatologist. They may be assembled in a retail store from a set of ingredients by a knowledgeable clerk. Systems or sets of cosmetic creams or lotions with a wide variety of properties may be pre-manufactured and chosen based on a given customer's coloration, skin type, and specific needs. Further, cosmetic boutiques will allow customers to formulate their own materials by ordering cosmetics based on given selections of ingredients.

The main barrier to a general solution for custom manufacture and distribution of such topical agents is that there are many features that may be included in a given product, and the customer needs for particular end aesthetics, skin types and complexions are quite varied. It is not commercially feasible to manufacture and stock on a larger scale specifically User customized formulations with the granularity that would be optimal for a given User's needs. Further, customers of cosmetics are more and more interested in obtaining specific and personalized products which may be purchased on-line or in a retail setting. Thus, there is a growing need in the art to provide new systems and ways to provide useful compounds based on a determination of an individual's specific needs using, for example, advanced image analysis techniques, and formulations that are optimal for that set of needs.

Techniques to capture the reflectance spectra of a surface with moderate specular reflectance and predominately diffuse reflectance can require measuring the reflected color as RGB triplets, or measuring the reflected spectra of the surface using optical methods to integrate the reflectance with a known light source at a known distance with a detector that has been set to a fixed aperture, fixed integration optics, and measured over a fixed period of time. Devices that use these techniques are reflection spectrophotometers and colorimeters.

Some mobile devices have many of the characteristics of a colorimeter. For instance, they have a light source with known characteristics, a CCD detector, a processor, and a lens system that can be used for integration. However, until recently, the primary barriers to using mobile devices as accurate colorimeters are the need to: (1) control ambient light; (2) set the distance to the surface to be sampled; (3) control the aperture used for measurement of the sample; (4) control the detector sensitivity used for measurement of the sample; (5) control the time used for measuring the sample; (6) control the white balance for measuring the sample; and (7) control the focal plane for measuring the sample.

While cameras used in mobile devices have become the most popular handheld cameras presently in use, they lack the ability to manually set aperture, and the most popular devices do not allow software to set aperture, sensitivity, or exposure times. While the hardware and firmware of the mobile device may report what camera settings are used as data embedded in a resulting digital image file, techniques are often used within the firmware to enhance or improve the image, and adjust the white balance. The firmware that controls the camera has been optimized to produce quality snapshots, not to make reliable measurement of light and color. Such information, however, can be the basis for generating data for user-specific formulations. This gave rise to a need for systems and methods that address these issues and allow a user to capture accurate, repeatable color samples using a mobile device.

One such patent is exemplified in U.S. Pat. No. 9,122,919 of the present applicant, and products produced by MATCHCo. that allow for the creation of Custom Topic Agents formulated for specific customers using input gather interactively from a mobile device, processed using algorithms disclosed in that patent, and manufactured from a small number of primary components. It describes a system and method for specifying and formulating topical agents that are optimized for the characteristics of a particular individual by using image analysis techniques applied to photographs taken by a mobile phone, tablet, webeam, digital camera, gaming consoles, televisions, smart glasses, and other consumer or professional devices having an image sensor.

In one embodiment, the system generates a specification for a customized topical agent, referred to in that patent as an "Optimized Aesthetic Protective Topical Agent," or OAPTA. Such OAPTA in U.S. Pat. No. 9,122,919 is formulated for the needs and characteristics of a specific individual client, referred to in that patent and herein as a "User." The OAPTA may include a number of possible components. The components may include, for example, topical bases, water, emulsions, gels, gums, moisturizing agents, ultraviolet (UV) filtering agents, opacity agents, color control agents, reflectance control agents (i.e., for more or less shine, matte, or opalescent finishes), anti-inflammatory agents (such as, for example, aloe and the like), protective agents (e.g., vitamin E and similar materials) or other cosmetic components. The system described detects using the photograph generated and optical data (both data collected in the system and user-specific data all compiled in a database) and stores the information include individual User files having a specific identification code and password. The User's data is processed including the User's specifications and facial data so as to match their complexion to an existing referenced complexion to which a cosmetic formulation has already been defined (either based on a particular referenced user or a ground truth data set, or the like) and Users can also become reference users.

The patent notes that the stored information can be used to prepare a manually compounded OAPTA product or by use of a device which will automatically compound the product using the instructions given in the stored OAPTA data, including automated equipment which may be arranged in various geographic areas. U.S. Pat. No. 9,122,919 further discusses that OAPTA products may be compound on demand, or alternatively compounded in advance by making the most common formulations and including them in stock for faster turnaround time.

U.S. Pat. Nos. 8,593,634, 8,564,778 and U.S. Publication No. 2014/0081463 each disclose an apparatus for formulating specialty cosmetics, which include a set of machine readable instructions and firmware located upon a custom cosmetic blending machine. The instructions enable custom color mixing based upon a skin color measurements obtained from a general spectrophotometer device, and the custom color mixing instructions also control a plurality of peristaltic pumps. The pumps are connected to flexible tubing which connects to canisters. The apparatus includes a needle nozzle such as a bent needle nozzle each of which is attached to a peristaltic pump which nozzles direct fluid to a center section of a consumer container. The canisters are attached to canister caps and have strainers to keep foreign material out of the bent needle nozzles. The apparatus also includes a sanitary elevator and tub, the latter for storing alcohol and the sanitary elevator able to raise the tub to contain the bent nozzle needles when not in use. The elevator includes a sensor to measure the height of the tub to position it at an elevation for storage. The apparatus also has a heater and a fan to maintain temperature.

U.S. Pat. No. 5,903,465 teaches a dispensing machine for making customized cosmetics at point of sale to a customer. The machine of the invention includes a mechanism for receiving operating instructions about a customer's optimal formula, as well as dispensers having different cosmetic compositions. The machine has an activation mechanism for dosing to a common dosing chamber certain of the cosmetic compositions and at certain concentrations according to operating instructions provided. The mechanism delivers a dosed formula into a container to the customer as a cosmetic product. The system can include a temperature regulation system, dual pumps of different capacity, a bar code labeling system, and a telemodem for remote reporting of machine failure, empty dispensers and customer information.

Further issues arise in creating custom cosmetics and other-the-counter (OTC) products in that Good Manufacturing Practice (GMP) and OTC manufacturing requirements require that in manufacturing and filling of products, two individuals must sign off on every manufacturing step or a validated software system can be employed that can be used in conjunction with a qualified individual's sign off.

In processing such specialty formulations, a need has arisen for a method, apparatus and system for on-site compounding of user-specific data to make cosmetic custom formulations for Users. There is further a need for an apparatus and system in which they system can retrieve and display dispensed weights for each primary component, such that a single qualified technician can validate the dispensed weight in the system which automatically retains the weight and technician's signature, and a need for optimized delivery of such components for dispensing.

BRIEF SUMMARY OF THE INVENTION

The invention herein includes a system with associated apparatus and components for preparing a custom cosmetic formulation. The system comprises a controller in electronic communication with an order management system, wherein the order management system stores user-specific data including data related to a custom cosmetic formulation and components thereof; a plurality of valves for receiving pressurized fluid, the plurality of valves in electronic communication with the controller; a plurality of dispensers, each having a valve for metering fluid in predetermined quantities, and each having a dispensing head having a nozzle, each nozzle comprising a nozzle tip on a distal end thereof, wherein the nozzle tips are arranged so as to dispense a fluid into an inlet of a product receptacle, the dispensers in electronic communication with a data port; a measuring device in electronic communication with the controller, the measuring device capable of capturing data related to dispensed fluids from each of the plurality of dispensers and transmitting the data related to the dispensed fluids to the controller; a barcode scanner for reading order-specific instructions; a user interface for operator communication with the order management system and with the controller; a plurality of fluid conduits for introducing fluid to the dispensers; a fluid delivery apparatus for delivery of components of a custom cosmetic component to the dispensers; and a pressure source for pressurizing fluid in the fluid delivery apparatus for delivery of fluid from the fluid delivery apparatus to the plurality of dispensers.

In one embodiment of the system noted above the controller may comprise at least one microcontroller, which microcontroller may be configured to receive data from the order management system, comprising dispensing instructions; one or more of user-specific component property data for each component of a custom cosmetic formulation; and user-specific and/or operator-specific identification data.

In another embodiment of the system, the plurality of valves for receiving the pressurized fluid are solenoid valves. Preferably there are four solenoid valves and each is a three-way solenoid valve, and wherein there are four dispensers. The system may further comprise a relay shield in electronic communication with each of the plurality of solenoid valves and with the controller. In such an embodiment, the pressure source may be compressed air delivered through a series of compressed air conduits and the solenoid valves cycle compressed air to actuate the plurality of dispensers. The solenoid valves may also be actuated independently in response to a signal from the controller.

In an alternative embodiment, the dispensers may be canister dispensers, wherein the canister dispensers are arranged in a cassette, the cassette having a data port and being removable from the system.

In further embodiments of the system, the fluid conduits and/or the compressed air conduits may be flexible tubing.

In one embodiment, the barcode scanner may be a camera having quick read barcode scanning functionality. The barcode scanner may also be capable of receiving operator sign-on and identification information.

In preferred embodiments the user interface may be a graphical user interface, such as a touchscreen.

The system herein may have embodiments in which it further comprises a nozzle tip holder. The nozzle tip holder preferably comprises a nozzle tip holder body defining openings longitudinally extending therethrough to hold each of the nozzle tips so that each tip is positioned to dispense over or within an opening into a neck of a receptacle having a longitudinal axis therethrough for receiving a dispensed fluid and each nozzle tip is at an angle with respect to the longitudinal axis of the receptacle, but each nozzle tip is not in contact with any other of the nozzle tips.

In an embodiment of the system herein, the data captured by the measuring device includes at least one of weight data, volumetric flow rate data, and viscosity data.

In yet a further embodiment herein, the measuring device may be an analytical balance, which is preferably capable of capturing and communicating to the controller weight data as fluid is metered through at least one nozzle tip.

In a further embodiment of the system herein, the pressure source may be compressed air delivered through a series of compressed air conduits and the compressed air conduits are positioned to introduce compressed air into the fluid delivery apparatus.

The system may include a the fluid delivery apparatus which, in one embodiment herein comprises a first housing having an exterior surface and an interior surface defining an interior space, a removable lid, at least one pressure source inlet, and at least one fluid outlet; at least one flexible fluid container arranged in the interior of the first housing, wherein the at least one flexible fluid container has a puncture seal cap and a puncture seal fitting for engaging the puncture seal cap; a pressure controller for regulating pressure of a pressure source through the pressure source inlet; at least one fluid delivery apparatus conduit having a first end in communication with the puncture seal fitting and a second end for delivery of fluid through the at least one fluid outlet to one of the fluid conduits in communication with the plurality of dispensers. The flexible fluid container may be positioned within an outer container. There may be two flexible fluid containers, each positioned within an outer container and the first housing may accordingly have at least two fluid outlets, each of which is in communication with one of the fluid conduits leading to the plurality of dispensers. The pressure source in such an embodiment of the fluid delivery apparatus in the system may be compressed air delivered through compressed air conduits in fluid communication with the pressure source inlet.

In the system herein, the fluid delivery apparatus may comprises a plurality of housings, each of the plurality of housings having: an exterior surface and an interior surface defining an interior space, a removable lid, at least one pressure source inlet, and at least one fluid outlet; at least one flexible fluid container arranged in the interior of the first housing, wherein the at least one flexible fluid container has a puncture seal cap and a puncture seal fitting for engaging the puncture seal cap; a pressure controller for regulating pressure of compressed air through the pressure source inlet; at least one fluid delivery apparatus conduit having a first end in communication with the puncture seal fitting and a second end for delivery of fluid through the at least one fluid outlet to one of the fluid conduits in communication with the plurality of dispensers. There may be two flexible fluid containers in each of the housings, each of the two flexible fluid containers positioned within an outer container and the each of the housings having at least two fluid outlets, each of which fluid outlets is in communication with one of the fluid conduits leading to the plurality of dispensers.

The system herein may also preferably further comprise a mixing device, selected from a ball mill, a centrifuge, and a vibratory mixer.

The system may also further comprise a printer in communication with the controller for provided printed user-specific information, based on data from the order management system, to a receptacle for housing a custom cosmetic formulation. The printed user-specific information may be printed on a label placed on a receptacle for housing a custom cosmetic formulation.

The invention further includes a fluid delivery apparatus, comprising: a housing having an exterior surface and an interior surface defining an interior space, a removable lid, at least one pressure source inlet, and at least one fluid outlet; at least one flexible fluid container arranged in the interior of the housing, wherein the at least one flexible fluid container has a puncture seal cap and a puncture seal fitting for engaging the puncture seal cap; a pressure controller for regulating pressure of the pressure source through the pressure source inlet; at least one fluid delivery apparatus conduit having a first end in communication with the puncture seal fitting and a second end for delivery of fluid through the at least one fluid outlet.

The fluid delivery apparatus herein may have a flexible fluid container which is positioned within an outer container. In an embodiment herein, there are two flexible fluid containers, each positioned within an outer container and the housing includes at least two fluid outlets. There may also be two of the housings. In a further embodiment of the fluid delivery apparatus the housing may be generally cylindrical. The removable lid when closed is preferably sealingly engaged so as to be capable of pressurizing the interior space.

The invention further includes a method of preparing a customized cosmetic formulation, comprising: (a) providing an order management system having user-specific data related to a custom cosmetic formulation and components thereof; (b) providing a controller configured to receive the user-specific data from the order management system, wherein the controller is in communication with a user interface; (c) sending data from the order management system to the controller associated with an order for one or more custom cosmetic formulations, wherein the order is received in the order management system; (d) actuating a pressure source to pressurize a fluid delivery apparatus to deliver one or more fluid components of a first custom cosmetic formulation in the order to one or more of a plurality of dispensers, each associated with a fluid component of a custom cosmetic formulation in the order, wherein the controller actuates the pressure source; (e) dispensing a first fluid component from one of the plurality of dispensers into a receptacle for receiving a custom cosmetic formulation for a period of time associated with the data received by the controller; (f) monitoring a value associated with a property of the first fluid component by a measuring device in electronic communication with the controller while dispensing the first fluid component to confirm that the first fluid component is delivered to within a tolerance range of a predetermined value for the property associated with the first fluid component in the order and stopping dispensing of the first fluid component when the value of the property monitored is the same as the predetermined value or within the tolerance range; (g) recording a final measured property value for the first fluid component after stopping the dispensing of the first fluid component; (h) repeating steps (e), (f) and (g) for one or more additional fluid components in the order for the custom cosmetic formulation; and (i) mixing the one or more fluid components.

In the method herein the controller may include at least one microcontroller. The user-specific data may preferably comprise one or more of weight data for each component in the order for a custom cosmetic formulation, viscosity data for each component in the order for a custom cosmetic formulation, dispensing instructions, user-specific and/or operator-specific identification information, and operator-specific log-in information. The operator identification data may include log-in data so that an operator logs in through the graphical user interface for receiving dispensing instructions and data associated with the order, and confirms the weights of the components after dispensing for authenticating the order and for compliance with cosmetic formulation requirements. The user-specific information received by the controller, may be electronically communicated to a printer and incorporated into a quick read barcode printed onto the receptacle prior to dispensing the fluid components in the order for a custom cosmetic formulation. The method may also further comprise reading the quick read barcode using a camera having quick read barcode scanning functionality.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 5 is a longitudinal cross sectional view of a fluid delivery apparatus of FIGS. 6 and 8 taken along line 5-5 of FIG. 6;

FIGS. 5a, 5b, 5c and 5d are longitudinal cross-sectional views of the fluid delivery apparatus of FIG. 5 having fluids at different fluid levels within the flexible fluid containers in the housings thereof;

FIG. 6 is a transverse cross-sectional view of the fluid delivery apparatus of FIG. 5 taken through the lid thereof;

FIG. 12 is a cross-sectional representative view of an alternative embodiment of a dispensing apparatus for use with the embodiment of the system of FIG. 1 in place of the dispensing apparatus of FIGS. 9 and 9A.

DETAILED DESCRIPTION OF THE INVENTION

Figure 1:
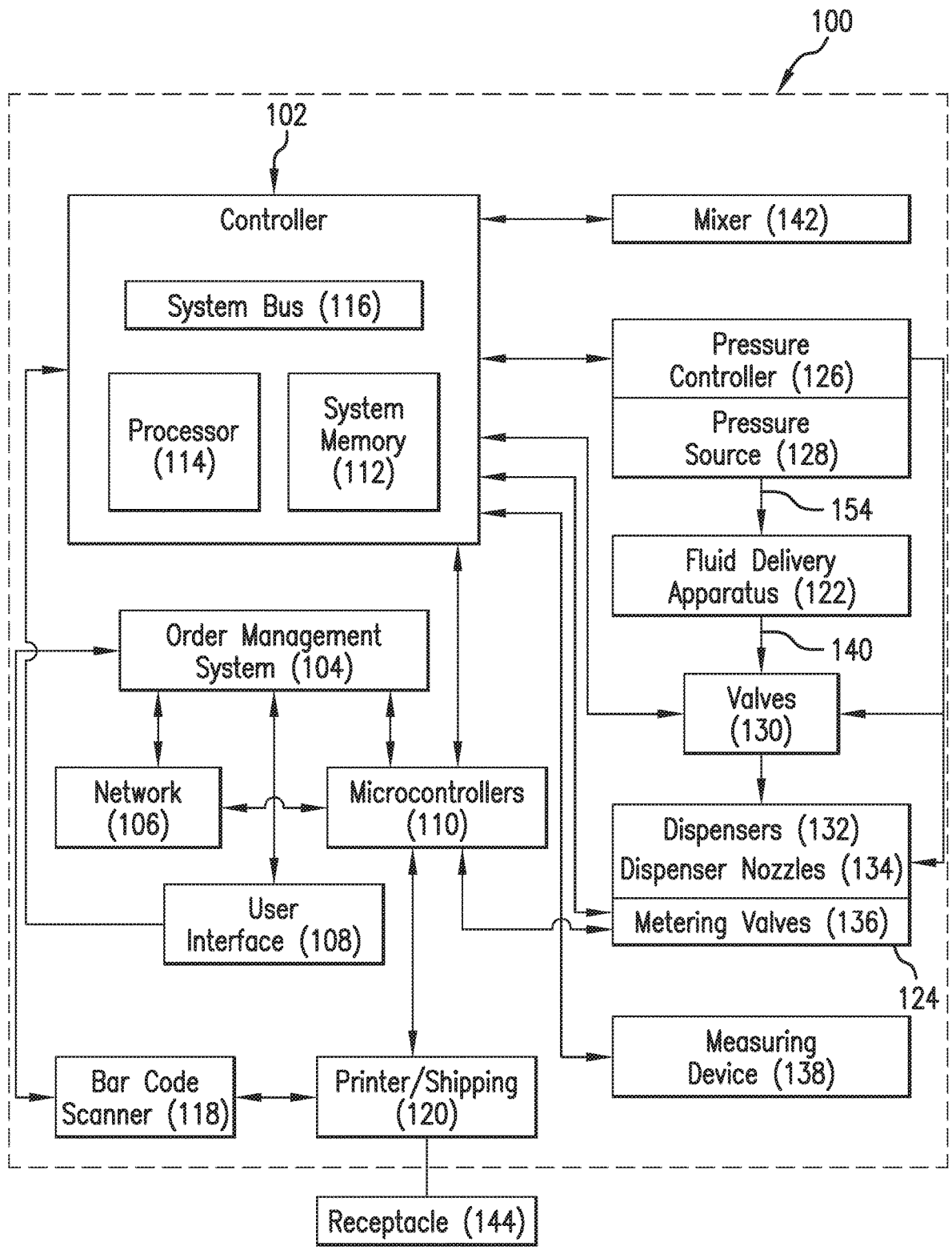
FIG. 1 is a representative flow diagram of elements of the system as described in a preferred embodiment herein.

With reference to the drawings herein, words of direction, such as "right" and "left," "inner" and "outer," "up" and "down," and "exterior" and "interior" are meant for reference purposes only and are not meant to be limiting in terms of the scope of the invention. Further, words in the claims and specification hereof are intended to have their ordinary meaning to one skilled in the art as amplified or clarified by any further application-specific information, in the absence of an express an applicant-provided definition.

The present disclosure includes a system and related method for preparing custom cosmetic formulations, as well as an apparatus for fluid delivery. In preparing custom cosmetic formulations, user-specific formulations are made requiring specified or predetermined quantities of fluid product components. As used herein, "cosmetic" is intended to include aesthetic cosmetic formulations (such as foundation, eye makeup, lotion, lip products, mascara, etc.) with a fluid base, as well as other over-the-counter (OTC) products in fluid form for topical application (sunscreen, foundation with sunscreen, medicated lotions, and the like). It also includes various components therein, including topical bases, water, emulsions, gels, gums, moisturizing agents, UV filtering agents, opacity agents, color control agents, reflectance control agents (i.e., for more or less shine, matte, or opalescent finishes), anti-inflammatory agents (such as, for example, aloe and the like), inflammatory agents (as used in lip plumper formulations for example), protective agents (e.g., vitamin E and similar materials) or other cosmetic components. The apparatus and system are designed to be directly applicable to OTC and GMP manufacturing requirements and provide an on-demand manufacturing and filling operation by allowing a single operator to enter data and sign off on the data, which information may be stored in the system, thereby obviating the need for multiple operators of the system to validate and sign off on each step. The system also allows for unit-level tracking and traceability, which are also important to OTC manufacturing requirements. The disclosure also includes an automated dispensing machine (ADM) with a unique bulk fluid delivery apparatus. The system and ADM are designed to maintain accurate and repeatable dispensing of a wide range of fluid viscosities and characteristics at various fluid pressures using variable dispensing data.

As used herein, "electronic communication" is intended to broadly mean that two components or elements can read, receive, transmit and/or communicate through any electrical signal, line, wireless connection, whether through direct plug-in, such as to a wall or dataport, USB, modem, or wireless/Bluetooth and the like as described further with respect to the systems herein and is not intended to exclude or limit the manner in which elements in the system, save, store, send, exchange, receive or send data or instructions.

As used herein, "fluid communication" is intended to mean the ability of a liquid or gas to flow through a conduit or series of conduits and/or intervening devices so long as the liquid or gas has the ability to flow through the system from one element to another element.

The term "custom cosmetic formulation" as used herein, means any specific custom formulation developed through any custom ordering system known in the art that uses a fluid base formulation, including those prepared at a point of sale using an independent scanner or reader, recommended by a technician or specialist, or those derived from specialty custom formulation system using data collected by a User and sent to a specialty system either through a device at point of sale, at an independent User location (home, office, etc.) using a User handheld device (scanner, phone with a camera, computer, and the like) or manually requested (such as by selecting from preferred lists of base components through a formulator website or specialty store or business). The term is not meant to be limiting but to encompass all such systems in which the cosmetic formulation is tailored to specific demands, requirements or characteristics of a User. One such formulation is described as an OAPTA in prior patents of the applicant, including U.S. Pat. Nos. 8,933,994, 9,122,918, and 9,122,919, each of which is incorporated herein in relevant part by reference.

A customized cosmetic formulation includes multiple components. Each such formulation may include a primary set of cosmetic components that may be mixed in different ratios to produce a custom cosmetic formulation, wherein each can vary in color opacity, the use of or level of UV protection provided, moisturizing or other agents related to skin dryness, emollients, emulsifiers, colorants and the like.

Systems have been developed for generating the information needed for preparing custom cosmetic formulations, including a User meeting with a technician who develops a personal formulation, or a User creating an electronic formulation through the use of entry of personal data in a cosmetic formulator's website, or through use of scanners and optical devices such as cameras, cell phones with cameras, computers having a built-in camera and other similar devices that capture an image and/or optical data associated with that image, and with various forms of facial recognition or identification software process the data to prepare recommended, user-specific cosmetic formulations.

The formulation from any such system, such as those described in U.S. Pat. Nos. 8,933,994, 9,122,918 and 9,122,919, incorporated herein in relevant part by reference with respect to the method described therein, include a server having a stored database of user-specific specific custom formulations, each corresponding to a user-specific identification code and having associated user-specific information as well as data related to the amounts of the components in the formulation, and the properties of such components (e.g., opacity, viscosity, density, weight and the like). In some systems, as noted in the above-referenced patents, and is the case in the MATCHCo.™ system, the User may log-in and re-order by way of the User identification information using the saved information in the User's user-specific profile. Such systems receive optical information from an associated optical device such as a camera that captures digital images of areas of a User's skin and related optical data, and compares that data to a database including known commercial formulations and/or a ground truth data set, and using such comparison matches the User's data with the stored data to create a specific custom cosmetic formulation. The design of a primary set of cosmetic components that may be mixed in different ratios to produce custom formulations that vary in color, opacity, ultraviolet (UV) protection, dryness of skin, and other qualities.

The process as set forth in U.S. Pat. No. 9,122,919 includes taking in a set of instructions describing a custom cosmetic formulation, and applying such instructions for the ornamentation of the custom product packaging and container. The interactive application of these instructions includes the measured deposition of each primary component into a container or receptacle. As used herein, "receptacle" is intended to mean any receiving device, including container, bottle, bowl, labware, jar, cup, tray and the like, and is preferably an approved container for use with cosmetic products. Then the components are blended or mixed within the container to form a uniform mixture. The method involves organizing and designing primary components to make them easy to design and use in custom cosmetic formulations and to deliver to a receptacle.

In preparing such formulations, primary components may be liquid components that are formulated followed by addition of solid components prior to mixing, or more preferably, instead of using all individual raw ingredients such as iron oxide, or titanium dioxide and the like as primary components each added individually, primary components may be to some extent pre-formulated in liquid form for use as functional standalone cosmetic agents that are then the primary liquid components to be used in preparing custom cosmetic formulations according to the present invention. They are preferably fluid for ease of mixing and delivery. The primary components may be each of different colors or monochromes, such as black, yellow, white and red, and other colors with various components optionally pre-mixed into the primary component, or may each have the same color such as those above or an only slightly different color and/or or each including different additives. Such primary components can be supplied in bulk in such a manner. This allows the design of a system that can more readily use such primary components selected for similar viscosities to mix, allowing for primary components to meet the same or similar regulatory constraints. It thus allows primary components to be designed for easy blending.

Thus, the components in a custom cosmetic formulation herein, while they can each be discrete components, are preferably components that are already themselves functional standalone liquid cosmetic agents. It is within the scope of the invention to use such liquid cosmetic agents as primary components to create formulated color components that run the color gamut, as each is a liquid and a functional standalone custom cosmetic agent. It is also possible to formulate each of the primary components developed in this manner in advance to include specialty additives where desired for incorporating into the custom cosmetic formulations, such as a UV blocking additive (organic or inorganic), an opacity agent, a thixotropic agent, an emulsifier, cleansing agent, fragrance agent, moisturizing agent, exfoliating agent, sunless tanning agent, and other specialty additives incorporated in a user-specific formulation. Preferred criteria for such primary components are that each may be a standalone cosmetic agent as described above, each may have known regulatory qualities, each may have a viscosity selected to be compatible with other primary components, each may blend well with the others, and each describes some maxima of a custom quality. The viscosity, flow characteristics, volumetric flow rate and custom quality type of each primary component may be known or determined, and digitally saved in the custom cosmetic formulation server as the primary component properties for the components in the custom cosmetic formulations.

The user-specific data stored in the database in a storage area of a server of such a system (or individually entered by a customer and submitted to the server or a further, separate server) are part of a user management system that can be used by the invention herein to prepare a custom cosmetic formulation. In addition to the component property information, the instruction data from the order management server preferably includes the ratios of the components, which may be expressed as the weight or weight percentage of the component based on the total weight of the component in the formulation. Other information to be stored in the order management server include preferred shipping information for the custom cosmetic formulation, information useful for customizing the receptacle for the formulation (i.e., information for specialty printing on the receptacle or on a label intended for placement on the receptacle, wherein such information may include, e.g., brand name, product name, color name and/or a User name), and information related to the scan or digital images that were used to create the custom cosmetic formulation, User identification information (name, address, preferences, phone number, email, skin type, makeup preferences, etc.), and operator information (operator name, address, identification number), as well as order numbers, pricing information (discounts, multiple use specials, taxes, etc.).

A system for preparing a custom cosmetic formulation, based on the custom cosmetic formulation data and using primary components as discussed above as the components of a custom cosmetic formulation, and a method for preparing a formulation are now further described herein.

A general flow chart showing the elements of the system and overall method steps is shown in FIG. 1, wherein the system is shown generally as system 100, with the relevant method steps identified along with the elements of the system as noted and the status of an order being processed is further identified in FIG. 1 as shown. Initially, the controller 102 and order management system 104 as well as other useful software interfaces for use in the overall system 100 herein are described below, followed by a description of other apparatus elements in the system 100 and the associated method steps.

In the system 100, a controller 102 is provided having an order management system 104. The controller may be any suitable controller capable of providing information or data to other components and receiving, storing and processing such information through a system memory 112 using one or more suitable devices or systems for memory storage and one or more system processor(s) 114. The controller preferably includes a processor 114 which may be a standard computing processing unit (CPU) as well as standard operating system or cloud based system in communication with a local controller in combination. The computer preferably also includes a system bus 116 which may be incorporated in a CPU system hardware, or cloud-based through a network, the system bus having various locations for input and output of signals and information. The precise instrumentality may be configured in various ways to carry out the functions as required herein on the equipment and apparatus components as noted. The order management system 104 may reside on the same controller or on a separate server having a separate functionality, processing system and memory capacity. In a preferred embodiment the controller 102 may be or may include one or more microcontroller(s) working in communication either working with the controller 102 or with any cloud-based server(s) for data storage and for communication through a web-based network with the order management system.

An order management system is provided that preferably includes a server having user-specific data related to a custom cosmetic formulation and components thereof. A system is shown in a preferred embodiment in FIG. 1, however, other system arrangements that are suitable for carrying out the steps and functionalities described herein may be used. An order management system may include a server capable of having the capability to store and communicate user-specific data as noted above. Examples of such servers are described in U.S. Pat. Nos. 8,933,994, 9,122,918 and 9,122,919, incorporated herein in relevant part by reference, which describes implementation of an OAPTA Reference Service which may be a single or shared resource serving one more locations having similar automation equipment. It also may include an on-demand system allowing a User to create a custom cosmetic formulation with some products compounded also or alternatively in advance.

The controller 102 and order management system 104 may each be located so as to include appropriate hardware and software, e.g., each may reside and be executed on one or separate devices capable of running an operating system (OS) such as Microsoft® Windows® operating systems, the Apple OS X® operating system, the Apple iOS® platform, the Google® Android® platform, the Linux® operating system and other variants of UNIX® operating systems, and the like. The controller and/or the order management system may each be a web-based server system with associated executable software and memory capacity, such as one in which functions can be performed remotely, in the cloud, or via software-as-a-service, or a networked system with a local controller having a standard operating system, processor and memory communicating with a web based system as a controller. In one embodiment, a web-based server system such as system would include remotely connected servers and/or devices with remote functionality which can execute on server class computers having sufficient memory, data storage and processing capability and that run a server class operating system (such as Oracle® Solaris®, GNU/Linux®, and Microsoft Windows® family of operating systems). Such systems may include a plurality of software processing modules stored in the memory and executed by a processor. Such modules can be in the form of one or more suitable programming languages which are converted to machine language or object code to allow the processor(s) to execute the instructions. The software may be in the form of a standalone application, implemented in a suitable programming language or framework.

The method steps required to be carried out on the various system elements and devices can be performed using one or more programmable processors executing one or more computer programs to perform functions by operating on input data and generating output, and also by receiving and storing relevant data. Such steps may also be performed by, and apparatus actuated by use of special purpose logic circuitry, e.g., a FPGA (field programmable gate array) or an ASIC (application specific integrated circuit). Modules can refer to portions of the computer program and/or the processor/special circuitry that implements that functionality. Processors suitable for the execution of a computer program include, e.g., general and special purpose microprocessors. A processor will generally receive instructions and data from a read-only memory or a random access memory or both. The essential elements of a controller as that term is used herein to reference a computer (whether hardware or web-based with graphical user interface (GUI)), include a processor for executing instructions and one or more memory devices for storing instructions and data. Information carriers suitable for embodying computer program instructions and data include all forms of non-volatile memory, including, e.g., semiconductor memory devices, e.g., EPROM, EEPROM, and flash memory devices, magnetic disk, e.g., internal hard disks or removable disks, magneto-optical disks, and CD-ROM and DVD-ROM disks, solid state hard drives, and the like. One or more memories can store media assets (e.g., audio, video, graphics, interface elements, and/or other media files), configuration files, and/or instructions that, when executed by a processor, from the modules, engines, and other system components noted herein and that perform the functionality associated with the system components. The processor and the memory can be supplemented by, or incorporated in, special purpose logic circuitry.

In other preferred embodiments, in a web-based server and controller 102, a user device includes a web browser, native application, or both, that facilitates execution of the functionality described herein. A web browser allows the device to request a web page or other downloadable program, applet, or document (e.g., from the server or servers) with a web page request. One example of a web page is a data file that includes computer executable or interpretable information, graphics, sound, text, and/or video, that can be displayed, executed, played, processed, streamed, and/or stored and that can contain links, or pointers to other web pages. In one implementation, an operator of the system, requests a web page from the server through the graphical user interface 108. Alternatively, the device automatically makes such a request with the web browser in response to an actuation request. Examples of commercially available web browser software include Microsoft® Internet Explorer®, Mozilla® Firefox® and Apple® Safari®, among others.

In some embodiments, operator devices will include client software which provides functionality to the device noted for the implementation and execution of the features described herein. The client software can be implemented in various forms, e.g., it can be in the form of a native application on the device, a web page, widget and/or Java, JavaScript, .NET, Silverlight, Flash, and/or other applet or plug-in that is downloaded to the device and runs in conjunction with the web browser. The client software and web browser can be part of a single client interface on one device, or can be implemented as a plug-in to the web browser or to another framework or operating system. Other suitable client software architecture, including but not limited to widget frameworks and applet technology can also be employed with the client software.

A communications network 106 can connect various devices used herein in electronic communication with the controller 102 and/or the order management system 104, which network can also be in electronic communication with a user interface 108 such as an electronically actuated analog interface, graphical user interface or other suitable user interface. Suitable networks include operation over media such as standard telephone lines, LAN or WAN links (e.g., T1, T3, 56 kb, X.25), broadband connections (ISDN, Frame Relay, ATM), wireless links (802.11 (Wi-Fi), Bluetooth, GSM, CDMA, etc.). Other media may also be used. The network preferably can carry TCP/IP protocol communications, and HTTP/HTTPS requests made by a web browser, and the connection between the clients/device and servers can be communicated over such TCP/IP networks. Other communication programs may also be used as are known or to be developed in the art.

The controller 102 and order management system 104 may also be practiced in distributed computing environments wherein tasks are performed by remote processing devices that are linked through a communications network 106. In a distributed computing environment, various program modules can be located in both local and remote computer storage media including memory storage devices. Various types of system hardware and software other than that described herein may also be used, depending on the capacity of the devices and the amount of required data processing capability. The system can also be implemented on one or more virtual machines executing virtualized operating systems such as those mentioned above, and that operate on one or more computers having hardware such as that described herein. In some cases, rational or other structured databases can provide such functionality, e.g., a database management system which stores data for processing. Examples include, MySQL® Database Server or Oracle® Database Server, the PostgreSQL® database Server, or the DB2® Database Server.

It should also be noted that implementation of the system and method herein can be provided and carried out on one or more computer-readable programs embodied on, or in, one or more devices. The program instructions can be encoded on an artificially-generated propagated signal, e.g., a machine-generated electrical, optical or electromagnetic signal, which is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of these. Moreover, a computer storage medium can be a source or destination of computer program instructions encoded in an artificially-generated propagated signal. The computer storage medium can also be or be included in one or more separate physical components or media (e.g., CDs, disks, hard drives, and other storage devices).

The controller or some aspect thereof, may include, be in communication with or be replaced with one or more microcontroller(s) 110. In one preferred embodiment, for example, at least one microcontroller 110 is used to interface with a web-based order management system and web-based system that is acting as a controller 102 for local control by the microcontroller of the dispensing application as described further below.

A preferred order management system 104 is incorporated in a cloud-based system controller (such as representative controller 102 in FIG. 1) having an Amazon® Webservices (AWS) server using an Elastic Beanstalk™ application service to automatically handle capacity provisioning, load balancing, scaling, and application health monitoring. Such a system may be supported by order management applications developed in Java®, PHP, .NET, Node.js, Python™, and Ruby™. Other similar cloud-based server systems having similar web-based service systems to those of AWS may also be used. The Elastic Beanstalk application service can be used to act as an application programming interface (API) for electronic communication with other devices and features of the system of the invention as described herein. The API communicates with other software useful for the present system, such as, e.g., EasyPost® API for generating shipping labels for sending the custom cosmetic formulation(s) to the User(s) noted in a given order. The API should also be able to communicate electronically with software related to other devices in the system, e.g., the dispenser application software described herein for dispensing primary components for and making custom cosmetic formulations.

A preferred order management system 104 as noted above preferably includes the AWS Elastic Beanstalk application as the application server and API, a Java® and Java® Spring Framework, as a database for receiving and storing information in system memory 112 which may be configured using various database software programs. One suitable such software compatible with the AWS API is an open source Sequel® (SQL) database management system software capable of managing the stored data in the database, such as MySgl™ and AWS DynamoDB™, however, other analogous web-based API's and associated databse software may also be used. System messaging may be provided by any suitable messaging software program, and preferably one that is compatible with the other software programs used. In the preferred system, AWS SQS messaging software may be used for communicating electronic messages to and from the database and the various components of the system herein. Such a database messaging system preferably also includes message storage software compatible therewith, such as AWS S3 software. The AWS API as noted above is also compatible with EasyPost® for generating shipping labels, and the like.

A further application module for use in the system in communication with the controller 102 and order management system 104 includes a dispenser application which is configured to read a barcode preferably using a scanner 118 and which is in electronic communication with the order management system 104. A preferred barcode for use herein is a quick read barcode, i.e., QR Code that may be employed to track and identify a user-specific order. Through this, it would also download the user-specific custom cosmetic formulation in an User's order for dispensing from the order management system 104. It dispenses the user-specific order and submits the results as recorded by an operator in the system through the controller and to the order management system. This dispensing module is preferably an application that employs, in communication with the controller, a microcontroller, such as a Raspberry PI, Arduino board, Beagle board, NXP development board, LattePanda board, or similar such device as a hardware microcontroller incorporating a Python application or other application suitable to run on the microcontroller selected. Microcontrollers used should have a suitable operating system, compatible software and preferably also electronically communicate with a readable software for barcode scanning. The microcontrollers like an Arduino board, Beagle board, NXP development board, LattePanda board and the like, may further may include a user interface, such as a graphical user interface, e.g., a Kivy Touch or the like. Similar modules operating on such a microcontroller may be employed not only in the dispensing step in conjunction with the various apparatus associated for dispensing fluid components but also at other various locations in the system as a part of or collectively as the controller herein.

The controller 102 and order management system 104 are also preferably in electronic communication with a print file render service module which may further be in electronic communication with a printer. Such a module can run as a cloud-based application and be used to receive AWS SQS messages to render receptacle print files. The print files are rendered using Adobe® Illustrator JSX scripting (or other suitable software) and may be saved to AWS S3 storage or other storage source. Such a module can run on any suitable virtual server having a suitable programming framework. Imaging may be effected by Adobe Illustrator variable printing. For example, a Topshelf® Windows® service framework may be used, with AWS SQS messenger and the AWS S3 storage. Print files may be downloaded for printing receptacles either directly on the receptacle or on a label through a further module in communication with the controller 102, order management system 104 and a printer 120, such as a print file downloader service. Such an application could run in production to provide notification of new print files by receiving instructions using AWS SQS messenger or similar software. The downloader service would immediately download such files and deliver them to a print holder folder. The downloader service application may be effected using a suitable programming framework, and by employing suitable storage and messaging services, e.g., AWS S3 storage and AWS SQS messaging.

An additional module may include a shipping application which is also preferably in electronic communication with the controller and order management system. The shipping application preferably reads QR Code or another barcode so that it can identify a user-specific order and related data therein such as user-identification data (name, address, telephone number and/or email address) and download a shipping label image from the order management system 104. Once that is done, the shipping application can print a shipping label on any suitable printer using Common UNIX Printing System (CUPS). Other printing software may also be used. The shipping application reads a QR Code or other barcode and preferably includes suitable barcode scanning software. It is also able to run on microcontroller such as those noted above.

As noted above, the web-based controller and associated microcontrollers electronically communicating with the order management system and associated applications as noted above create an operator friendly system in which the operator can access both the order management system and monitor, enter, retrieve and submit data throughout the system for preparing a custom cosmetic formulation and during the method through use of a single or multiple user interfaces 108 such as graphical user interface(s) 108. Use of a graphical user interface as user interface 108 may be one or more networked tablets, monitors, Kivy Touch devices, smart phones, or combined with the controller as an all-in-one device. However, analog actuation through buttons associated with electronic communication to the controller may also be used. Preferably, at least one graphical user interface is located in each production area near where equipment is located for operator convenience (such as a graphical user interface at the print and order download areas, in the dispensing and/or mixing areas). However, one single graphical user interface may also be used, and if so, is preferably portable such that the operator can carry or move the interface to different work areas if need be.

Before further describing apparatus within the system 100, the operator steps to be taken to complete an order for a custom cosmetic formulation will be generally described with reference to order process 200 shown in FIG. 2. The system runs based on downloaded instructions from the order management system 104 as described above, and wherein instructions may include property information associated with components in the formulation, such as a weight ratio or specific weight of primary components needed to make the custom cosmetic formulation (or viscosity data, volumetric flow rate data and the like), shipping information, as well as customized information for use on the container or packaging such as customer identification data (name, address, phone number, email, payment data and the like) and also operator data (operator identification and/or log in information for example).

The instructions may be read by the controller 102 using various devices as described above that interactively present a series of steps for an operator to follow and access through the user interface(s) 108. The controller computer may also send and receive information to a localized microcontroller or microcontrollers through operator action. A graphical user interface may coordinate with a separate apparatus such as a printer having its own hardware and software through associated software code and application modules as noted above to prepare packaging and a receptacle for the customized cosmetic formulation. In a preferred embodiment, user-specific text or imagery is printed or transferred to the receptacle and/or shipping labels for each order. The instructions may also cause a digital code, such as a barcode, to be printed or transferred either directly to the packaging, to a shipping label, to a receptacle or to a receptacle label as desired.

To initiate an order placed by a User and sent to the controller through messaging from the order management system, an operator accesses the order management system and downloads files in step 202 associated with a new order. The user-specific information enters the system. User-specific information received, such as the information noted above, may include shipping information, payment information and formulation data. The information is scanned into the system using the data provided by the order management system in step 204. The order status is then set in the system as "pending."

The operator then performs a quality review in step 206 of the data looking for any errors or anomalies as against other orders, prior orders for the same users or for missing information or false identification or payment information. If the order is correct and data satisfactory, its status is changed to "order reviewed." If there are errors, anomalies or problem data as noted above, the operator then changes its status to "hold" and investigates the order in step 206a. If the order is fixed after investigation, the order status can be updated to "order reviewed." If not, the order can be further investigated, including potentially contacting the User and/or the source of the information data in the order management software. If there is no way to correct the order, the order may be terminated and the order management system notified.

The reviewed order is then queued with other orders in step 208. While an order may be processed individually, it is more efficient and preferred to process orders in batches. The data is manually cycled and queued after download and the order status is changed to "queued." Once a batch of orders is queued, the operator can then download a front and back print file. Once the print file is in the system, in step 210, the receptacle is printed. Printing may be carried out by printing a label for the receptacle or printing on the receptacle itself. Front and back print fields are generated which each have dynamic images (e.g., name, date and barcode, such as a QRCode) and static images (brand logos, components, company name, bottle weight, etc.). As the print file downloads, the order status is changed to "printed."

Figure 2:
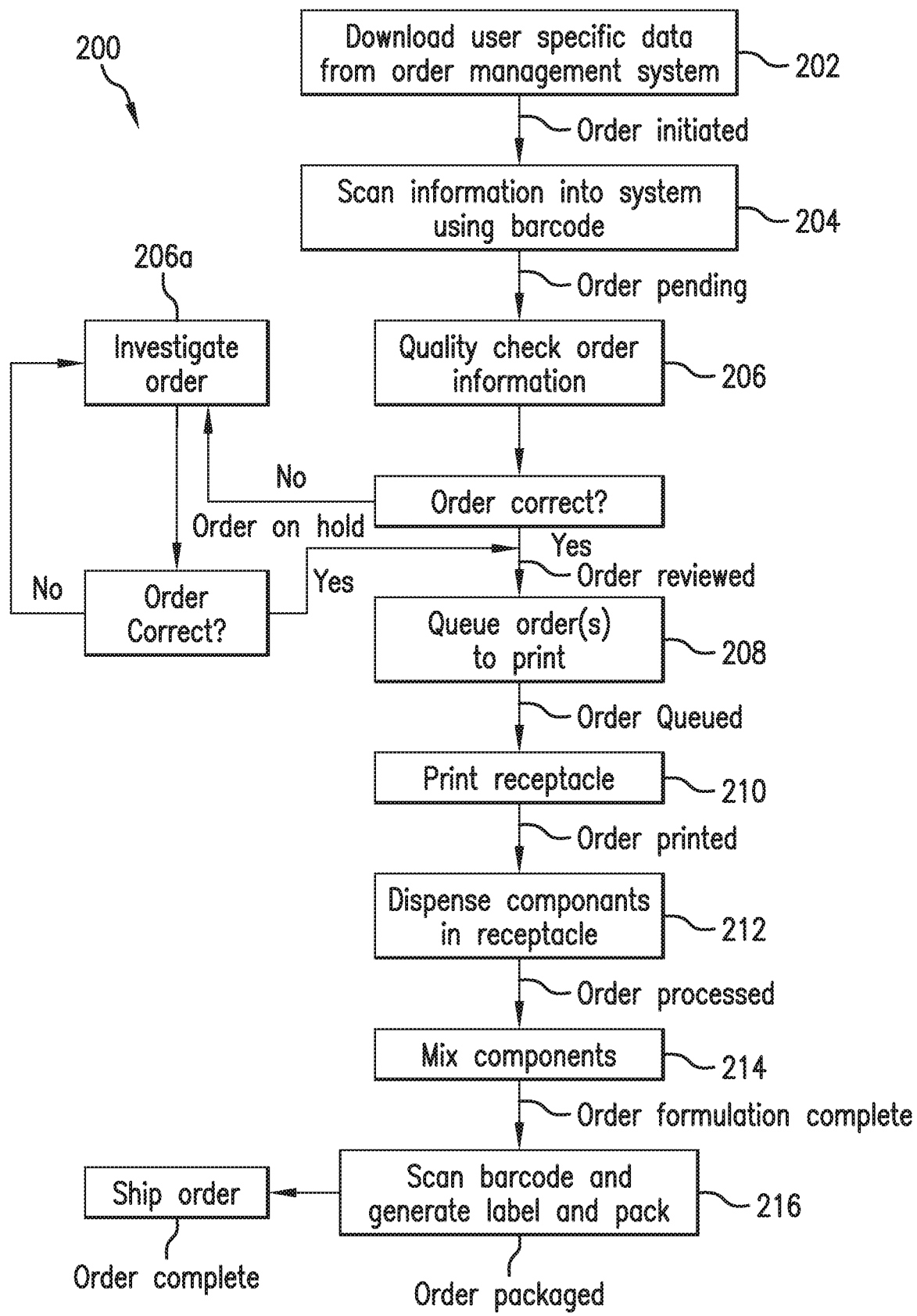
FIG. 2 is a flow diagram of operation of the embodiment of the system of FIG. 1 as described herein.

Using a dispensing apparatus 124, as referenced in FIG. 1, operating with a fluid delivery apparatus 122 in fluid communication with a pressure source 128 having and a pressure controller 126, in step 212 of FIG. 2, an operator dispenses fluid primary components to a receptacle associated with the order. The fluid primary components from the fluid delivery apparatus 122 pass through one or more fluid conduits 140 and are dispensed through solenoid valves 130 into dispensers 132 associated with the dispensing apparatus 124. Preferably, each dispenser 132 has a nozzle 134 and a flow control or metering valve 136 as described further herein. The nozzles 134 dispense primary components into the receptacle. While dispensing, the amount of primary component, the amount is monitored by data feedback on actual weight through use of a measuring device 138. A measuring device 138 may be, for example, an analytical balance or other device or instrumentation preferably in electronic communication with the system that is able to measure a fluid component property for controlling the amount of the component dispensed. For example, it may be any suitable balance that is capable of capturing and communicating weight data to the controller or any associated microcontroller as fluid is metered through at least one nozzle tip 180 on a nozzle 134 of a dispenser 132 as described in further detail below. It may also be a calibrated volumetric pump, flow meter or chronological device (such as a stop watch device), selection of which devices may depend on system design, data selected for metering, or the viscosity of the components.

Preferably, weight data and fluid component properties are communicated from and to the controller and recorded by the operator manually and/or electronically through a graphical user interface for authentication of the order and compliance with GMP manufacturing practices for OTC products. The metering valves 136 and valves 130, which are preferably pneumatic valves such as solenoid valves, are in communication with the controller, either directly, or through a microcontroller 110. Several such receptacles can be processed in a batch. After the primary components are fully dispensed in step 212 of FIG. 2, the order status is changed to "processed."

The processed order is then mixed in step 214 using a mixer 142 (which may be a ball bill, centrifuge or other suitable cosmetic mixing apparatus), and the order then includes a completed custom cosmetic formulation in each receptacle processed and mixed within the order, whether one or a batch of such formulations.

Figure 3:
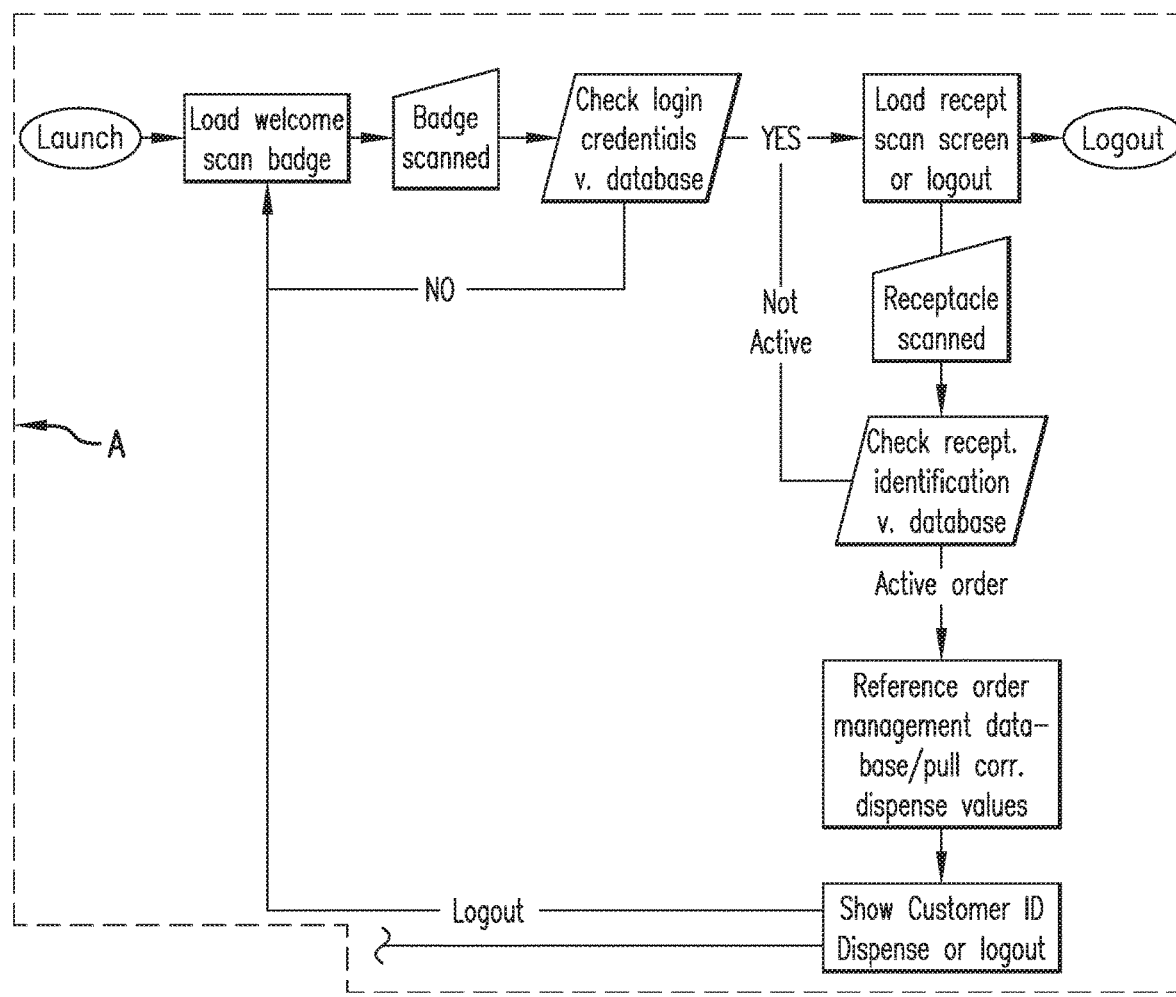
FIG. 3 is a software operations flowchart for fulfilling an order for a custom cosmetic formulation in accordance with the embodiment of FIG. 1.
Figure 3:
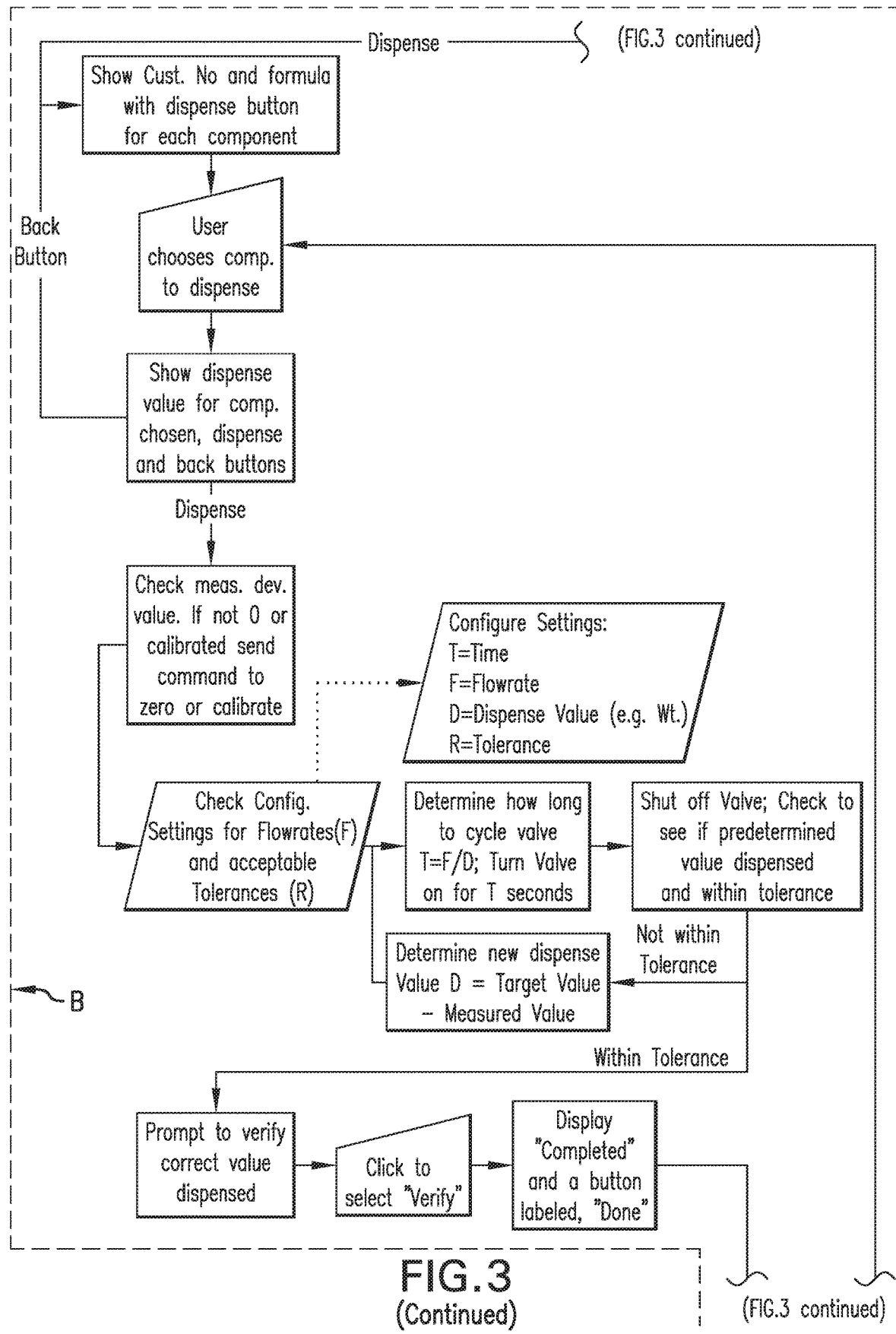
Figure 3:
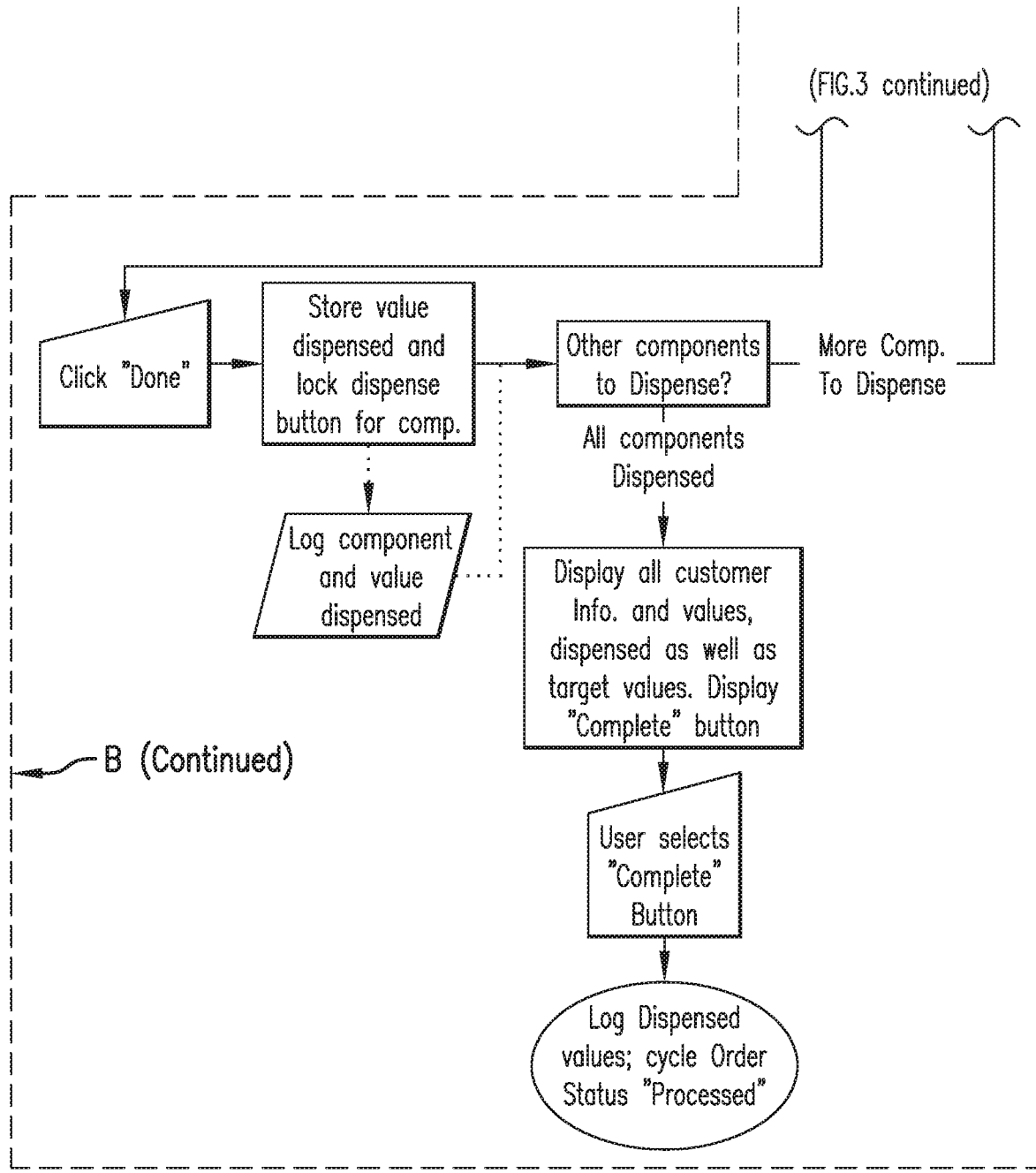
Figure 4:
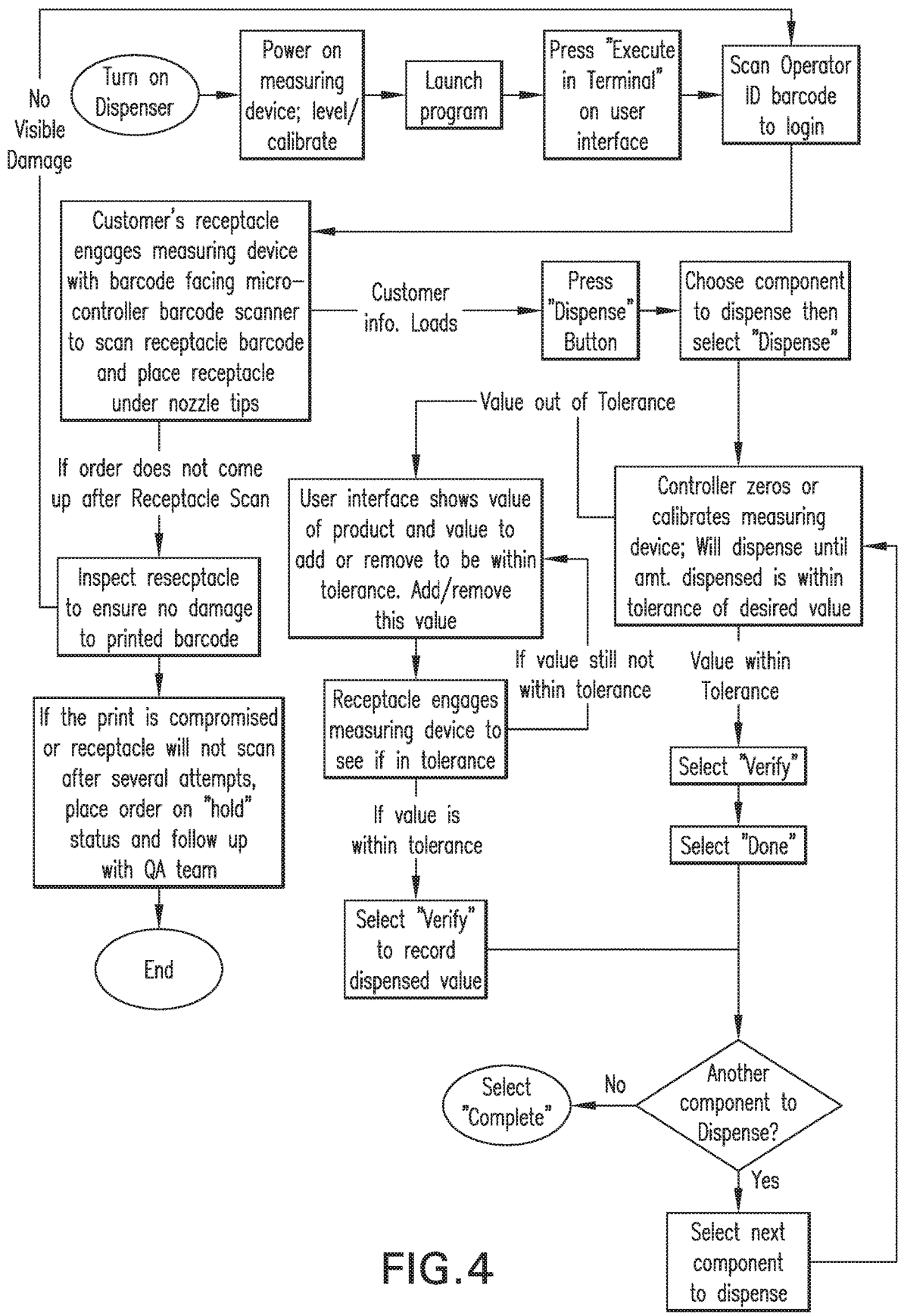
FIG. 4 is a flowchart of typical operations of fulfilling an order with the dispensing apparatus of the embodiment of the system of FIG. 1.
Figure 5C:
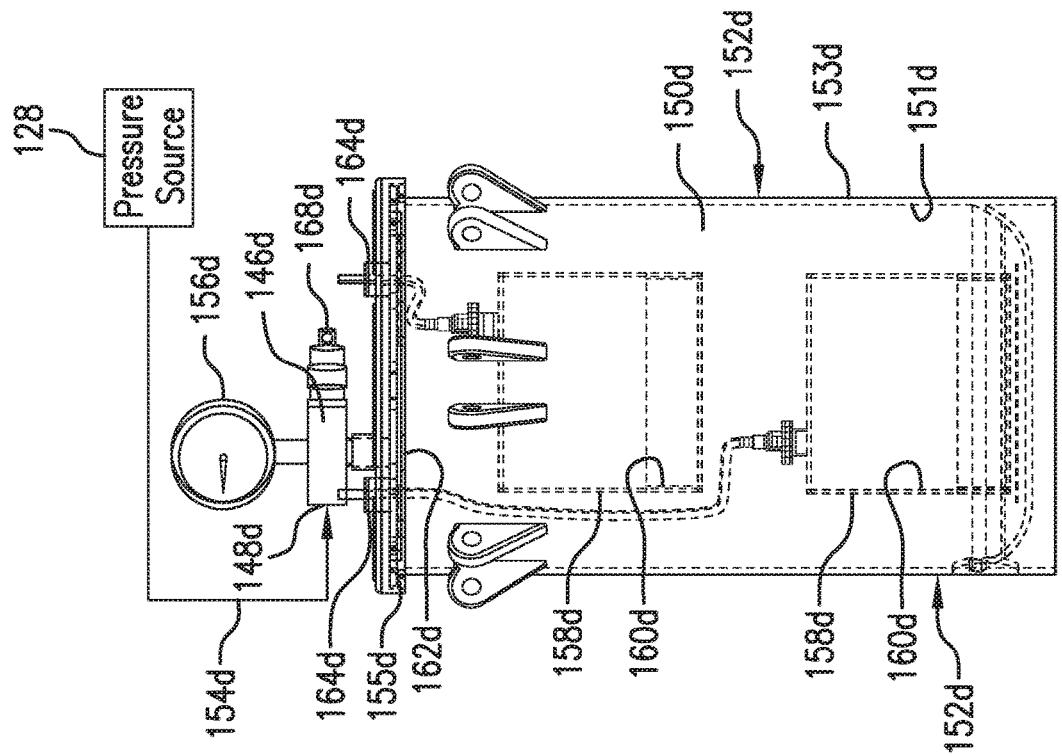
Figure 5D:
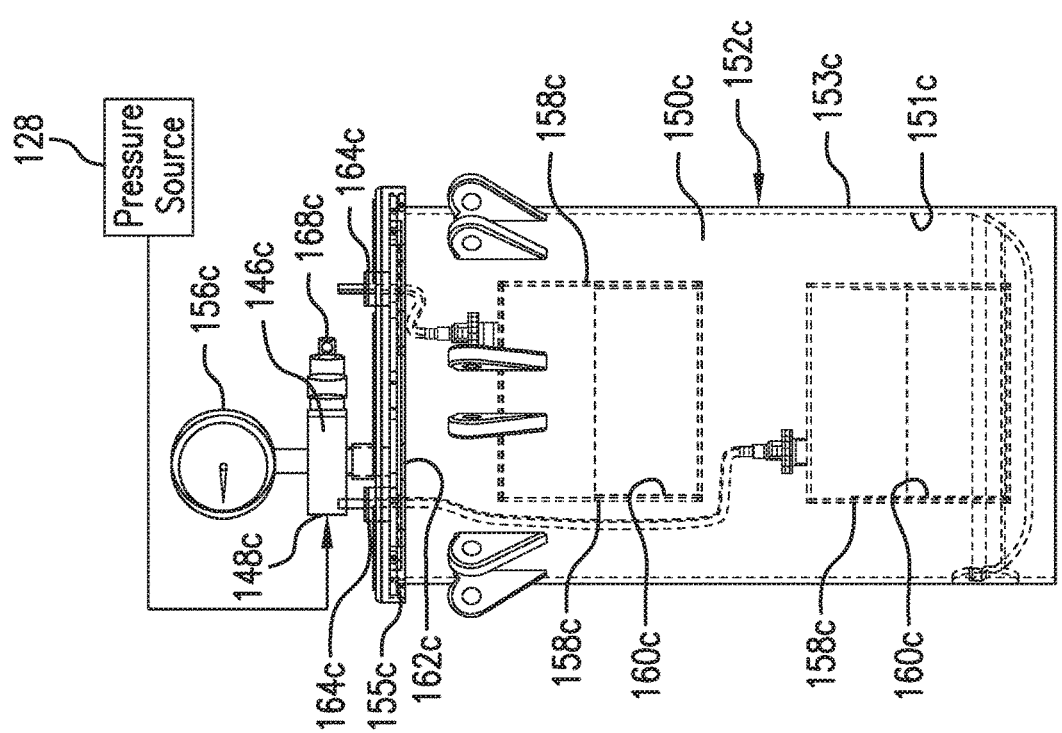

The mixed formulation is then preferably packed in step 216 by scanning the barcode associated with the custom cosmetic formulation and generating a label for shipping and preparing associated packaging. The shipping information may be provided to a shipping label using software applications associated with a printer as noted above, or may be printed on any specialty packaging using any of a variety of suitable print systems available commercially for packing and shipping. The order may then be preferably shipped in step 218 by the operator to a User or Users and the order is completed. FIG. 3 provides a software flowchart illustrating on example of software operations useful for fulfilling an order in a preferred system with the steps noted in area A associated with steps 202 to 210 and the steps in area B associated with step 212. FIG. 4 provides a flowchart illustrating typical use operations of fulfilling a customer order in a preferred embodiment specifically associated with a preferred dispensing apparatus.

The hardware and software associated with the system 100 is described above. The other apparatus and devices used within the system will now be further described. After the order download. The receptacle is printed and/or labeled with a printed label incorporating a user-specific barcode using a printer 120. The printer may be any suitable printer available commercially and may include system-specific settings and associated applications and software code available from the commercial printer. Suitable commercial printers for this purpose include, e.g., a Mimaki UJF 4042, or any other suitable UV printer, sublimation printer, inkjet printer and the like. The printed receptacle is then used by the operator to proceed to the dispensing process. In dispensing, fluid first must be delivered to the dispensing apparatus. A fluid delivery apparatus 122 is described below.

A variety of fluid deliver apparatus may be used provided it provides steady and controlled flow of primary components in fluid form to the receptacle through dispensers. Many such systems are known in the cosmetic arts, including automated nozzle dispensing apparatuses suitable for application of various cosmetic components to a receptacle 144. Other systems may include a forced pressurized feeding system using mechanical squeezing, peristaltic pumps, pressurized push rollers, and the like. A preferred apparatus 122 is described herein, but is not intended to be limiting with respect to the system 100.

With reference to FIG. 5, FIG. 6 and FIGS. 5a to 5d, a preferred fluid delivery apparatus 122 may be provided as a single device or as a set of a plurality of such devices having two or more fluid delivery apparatus 122 (shown in FIGS. 5a-5d as a set of four identical delivery apparatus 122a, 122b, 122c and 122d). Each fluid delivery apparatus 122 is for delivering a primary component of the custom cosmetic formulation. Each fluid delivery apparatus 122 (or 122a through 122d) incorporates a pressure source 128, which may be any suitable pressure source capable of pressurizing fluid in the fluid delivery apparatus for delivery of fluid from the fluid delivery apparatus 122 to one or more dispenser(s) 132. As shown and for operator convenience, and compliance with cosmetic manufacturing GMP requirements, a source of compressed or pressurized air 128 is provided. As shown in the drawings, each companion identical part is identified as associated with 122a, 122b, 122c or 122d by use of "a", "b", "c" and "d" but for convenience purposes, the individual parts will be described with respect to a general number, each of which is modified in the drawings with a letter corresponding to the particular fluid delivery apparatus. The precise number of units (one or more) may be varied by user design and system capacity. The pressure source may be "house" or lab introduced air in communication with a general compressed air system and/or an isolated compressed air cylinder or any other suitable pressure source. Preferably, compressed air from the pressure source 128 enters a receiving valve 146 in fluid communication with a pressure source air inlet 148 into the interior space 150 of a housing 152 having an interior surface 151 and an exterior surface 153. The pressure source air inlet may be any suitable design, and in one embodiment herein has a ¼ nuts per thread (npt) for connecting to regulated shop air for pressuring the housing. The air inlet, the receiving valve 146 and the interior space 150 are in communication through a compressed air conduit 154. Such conduit 154 as with the fluid component delivery conduit 140 may be flexible tubing, stainless steel conduit or hose, or other suitable delivery tubing. The pressure source preferably also includes a pressure controller such as valve 146 having a pressure gauge 156 for monitoring pressure into the system and keeping it at a stable level when the valve 146 is open.

The housing may be of a variety of shapes, including a cylindrical housing as shown, or may be spherical, a cube or a parallelogram shaped, and may be circular, square, rectangular or other shape as appropriate in longitudinal or transverse cross section. As shown, a cylindrical housing 152 having a rectangular longitudinal cross-sectional configuration and a transverse circular cross-sectional shape is shown. Suitable housings of this type include a pressure pot assembly as shown. Such a housing preferably has a removable lid 155 through which compressed air inlet(s) and/or fluid outlet(s) are provided therethrough. The lid 155 is preferably secured using a latch, lock, grommet or similar mechanism as are known in the art. A preferred lock may include a C-clamp with a T-handle as used with standard pressure pots.

The housing may be formed of a composite, polymeric or resin material, a metal or a metal alloy. It is preferred that whatever material is chosen that it is GMP compliant for use in providing cosmetic components for resale and is capable of sustaining applied pressure of up to about 250 psi. Preferably the housing 152 is stainless steel. The housing may incorporate a pressure relief valve 168 of any suitable configuration for relieving pressure from the interior space 150 of the housing in the event of any system failure or blockage. The preferred material is stainless steel as used, for example, in a stainless steel Graco 10 gallon pressure pot, however, other types of steel, other metals (such as iron), composites suitable of handling the pressure and other functionalities herein and the like as are known or to be developed in the art may also be used.

The interior of the housing may be of a variety of sizes as well. As shown in the cross section the housing is preferably about 1 foot to about 3 feet in height, preferably about 1.5 feet to about 2.5 feet, and most preferably about 2 feet in height, as measured in a longitudinal direction, and about 1 foot to about 2 feet in diameter, preferably about 1 foot to about 1.2 feet in diameter, as measured transversely through the housing. The wall thickness is preferably about 2 mm to about 10 mm depending on the material used. The size and interior may, however be varied.

The preferred embodiment is designed to hold two 11 in. by 11 in. outer containers as shown in FIGS. 5a-5d as outer containers 158. Two such outer containers 158 are positioned within each of the housings, although one or more housings may be designed with only one outer container or more than two outer containers. In addition, outer containers are optional. Each outer container 158 preferably includes a flexible fluid container 160 which is arranged in the interior of the housing and positioned within an outer container. The flexible fluid container preferably encloses a prepared primary fluid component. Such flexible fluid containers 160 may be used alone or stacked in optional outer containers 158 as shown. The flexible containers are shown as being within the outer containers. The flexible containers may be formed of a variety of materials such as polyolefin homopolymers or copolymers (e.g., polyethylene; polypropylene, high density polyethylene (HDPE) and low-density polyethylene (LDPE)), polyurethane homopolymers and copolymers; polyetherimides, and other suitable cosmetic or food grade polymers or materials.

Figure 7B:
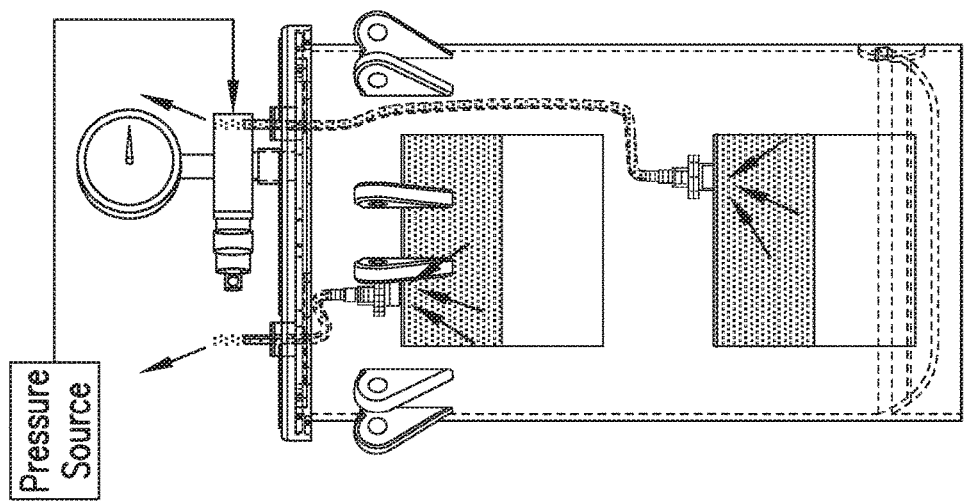
FIGS. 7a, 7b, 7c, 7d are the longitudinal cross-sectional views of FIGS. 5a-5d showing the flow of fluid and compressed air within the fluid delivery apparatus.
Figure 7A:
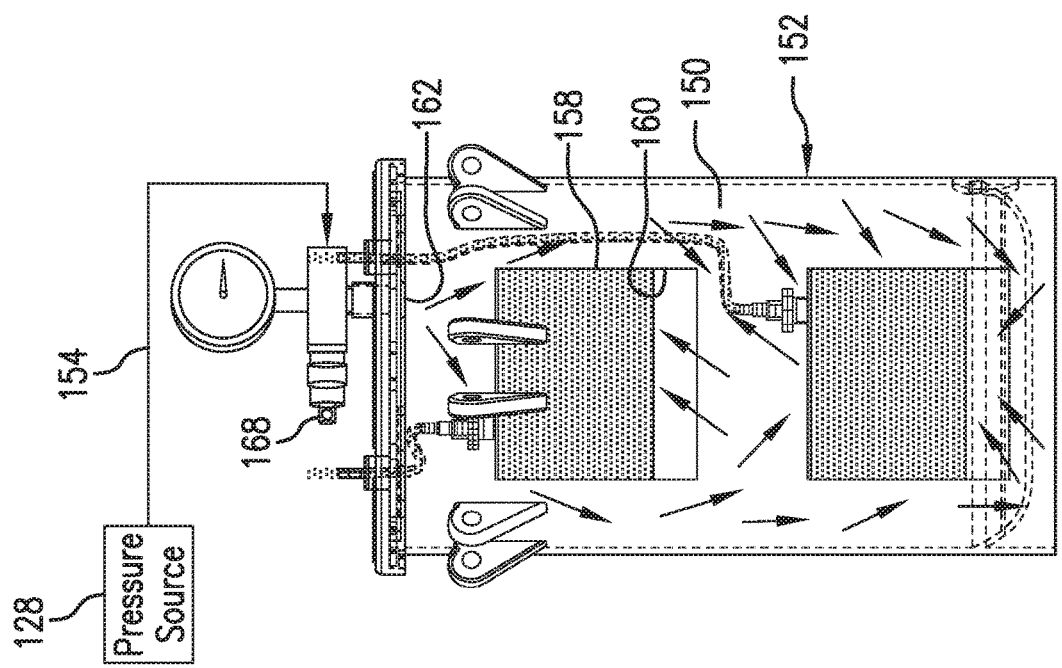

As shown in FIGS. 7a-7b, action of the pressurized air on fluid flow within the interior space 150 of the housing 152 is shown in a single apparatus in different states as shown in each of the figures. With reference to FIG. 7a, the flow of compressed air is shown by the arrows in this representative drawing. The air flows down from the pressure source through the housing compressed air inlet 162 it flows into the interior space 150 and around and compresses upon the outer containers and the flexible fluid containers. The pressure forces fluid in the flexible fluid containers upwardly.

Figure 7C:
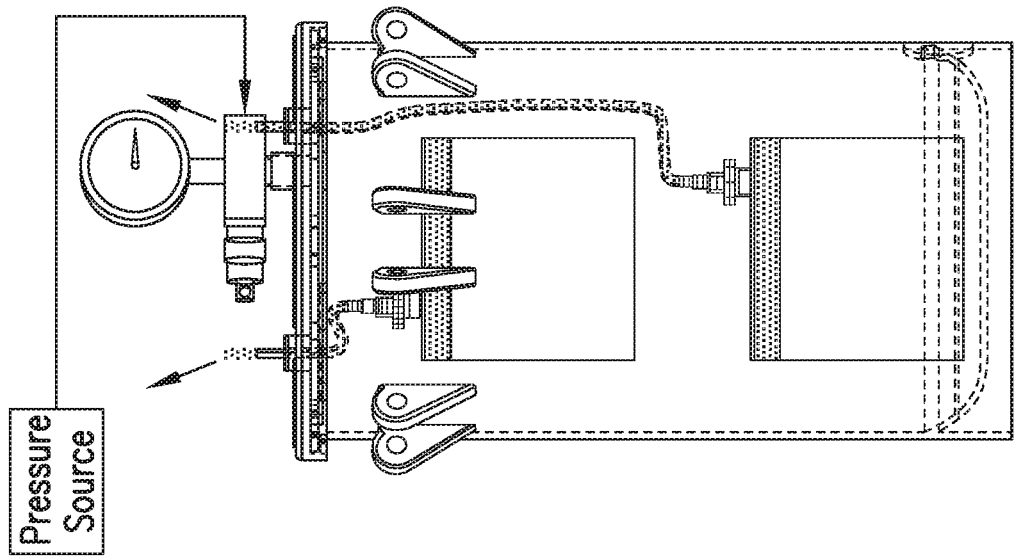
Figure 7D:
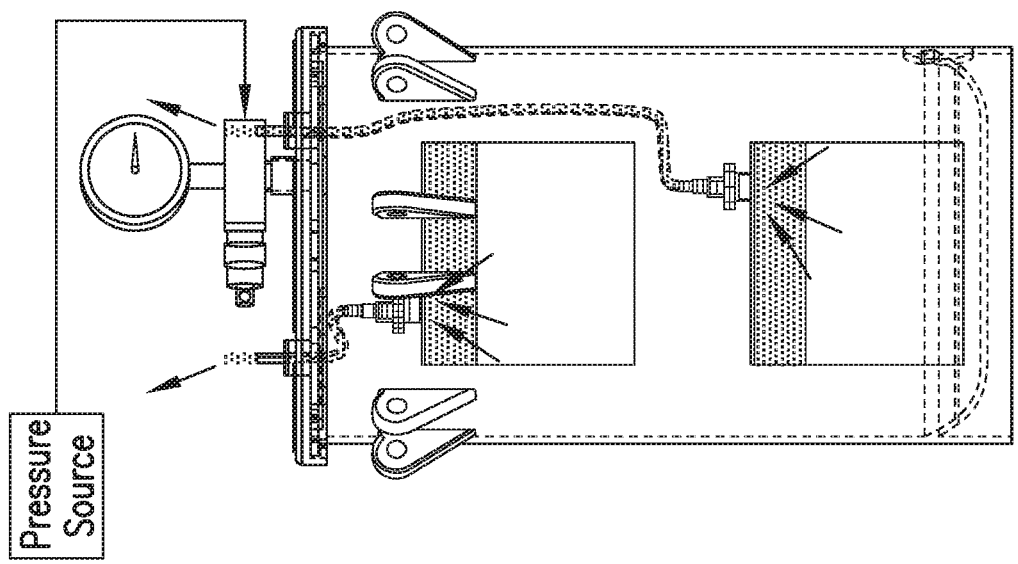
Figure 8:
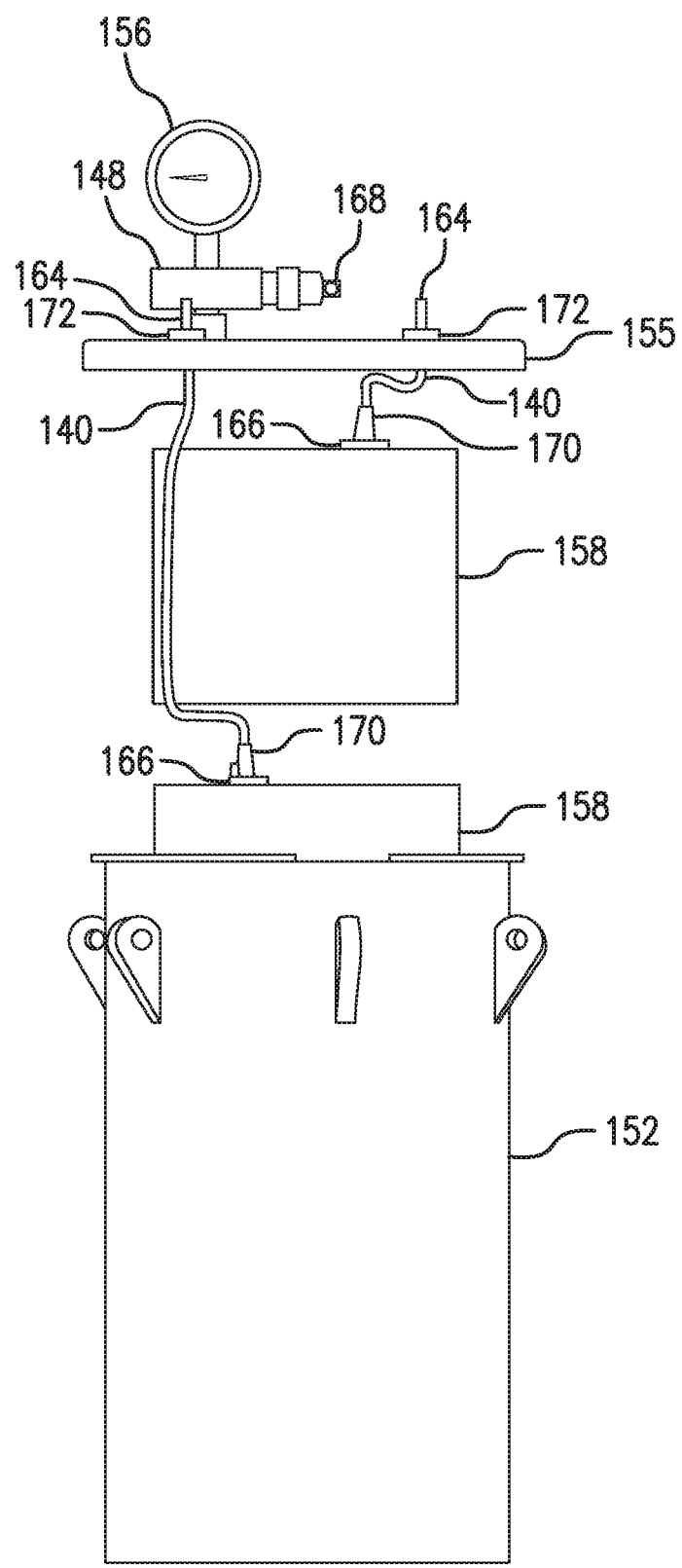
FIG. 8 is a perspective view of a fluid delivery apparatus according to the embodiment of FIGS. 1 and 5.

As shown in FIG. 7a air pressure forces the liquid (shown as a shaded portion) upwards leaving an air pocket beneath. In FIGS. 7b-7d, the flow of the fluid primary component in the flexible fluid container is shown by fluid flow arrows wherein the pressure pushes the fluid upwards through a fluid outlet 164 in the housing. As shown, a separate outlet 164 is provided on the housing for each flexible fluid container and flexible fluid conduit which are part of the overall fluid delivery conduits 140 that extend from a first end 140a in communication with the puncture seal fitting 170 described below to a second end 140b for delivery through at least one housing fluid outlet 164 to one or more such conduits in communication with the dispensers 132.

The conduit 140 thus runs from the flexible fluid container to and through the housing fluid outlet 164 and to the dispensers.

The flexible fluid containers preferably each have a puncture seal cap 166 and a puncture seal fitting 170 for engaging the puncture seal cap. The two may engage by mating threads, snap-lock fittings, and any suitable means for a leak free engagement that can withstand pressurization. The puncture seal cap on the flexible fluid container sits on threads that are provided on the flexible fluid container as preferably received as a commercial flexible fluid container. The puncture seal cap should have threads that mate with threads on the flexible fluid container (essentially the cap allows for connection of a bag-in-a-box outer container and inner flexible fluid container configuration which is preferably purchased commercially as stock materials for primary fluid components to the fluid delivery conduit 140). A fitting 170 is provided that then allows for connection of the puncture seal cap on one end and on the other includes a barb allowing for connection to the fluid delivery conduits. Such fittings, conduits and caps may be modified for different containers and different connection designs provided. As shown, in a preferred embodiment, conduit is preferably about 0.5 ID flexible tubing. Such flexible fluid containers may thus be pre-stored in a sealed manner, and the puncture cap installed to fit with puncture seal fitting 168 when loading new fluid components for delivery.

The internal tubing that is part of the overall fluid delivery conduit 140 exits the housing from each outer container through a push that connects the internal tubing to a pass-through housing fluid outlet fittings 172 installed on housing fluid outlets 164.

The flexible fluid containers 160 can be provided directly from a vendor or loaded manually. As shown in FIGS. 5*a-d* and 7*a-d*, four housings are provided to load two each of flexible fluid containers. In a preferred embodiment, four separate primary fluid components, which as discussed above may be varied to be of the same or different fluid base, each having the same or different additives (or no additives) and each may be unblended or pre-blended with other fluids or additives, and each may be of the same or different colors. For exemplary purposes, four different monochrome colored bases (e.g., white, yellow, red, black) each of which may be pre-blended may be introduced. The fluid components, the size of the housing and number of containers provided may be varied so that additional supply of components for longer delivery and operator time in between changing out of primary component containers may be achieved.

Figure 9:
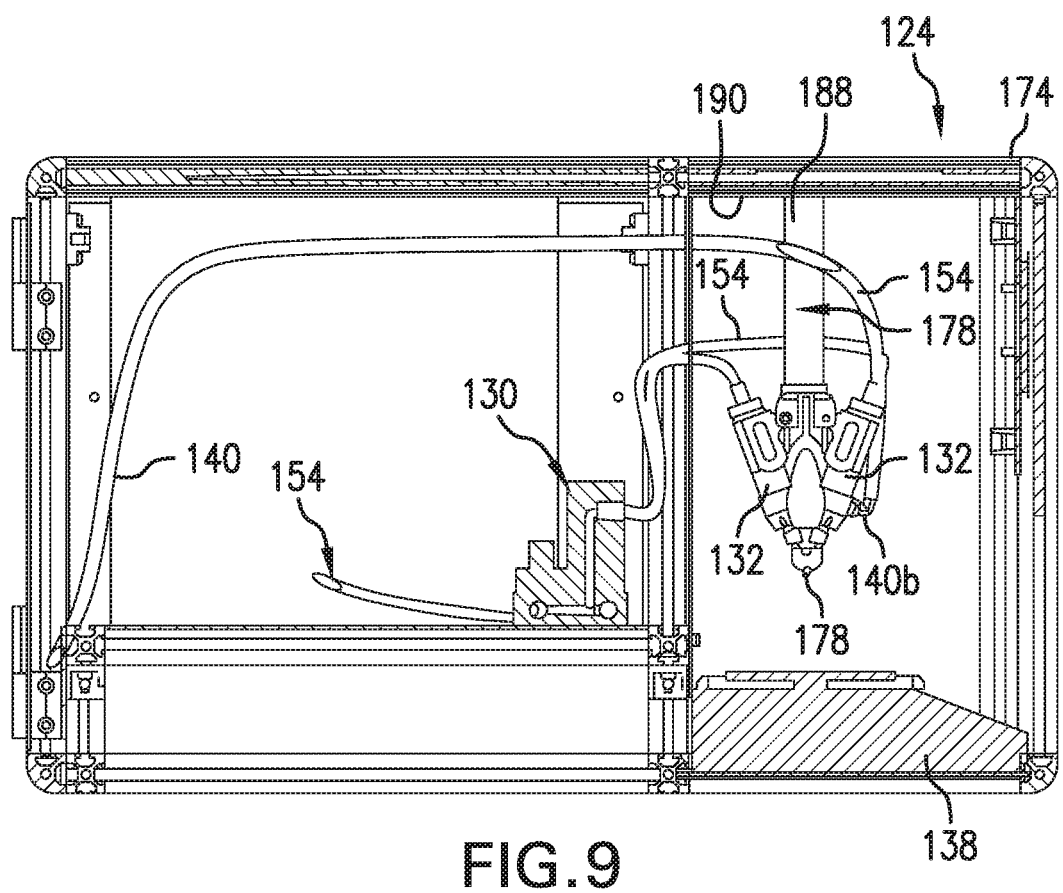
FIG. 9 is a longitudinal cross-sectional view of a dispensing apparatus according to the embodiment of the system of FIG. 1 taken along lines 9-9 of FIG. 9A.
Figure 9A:
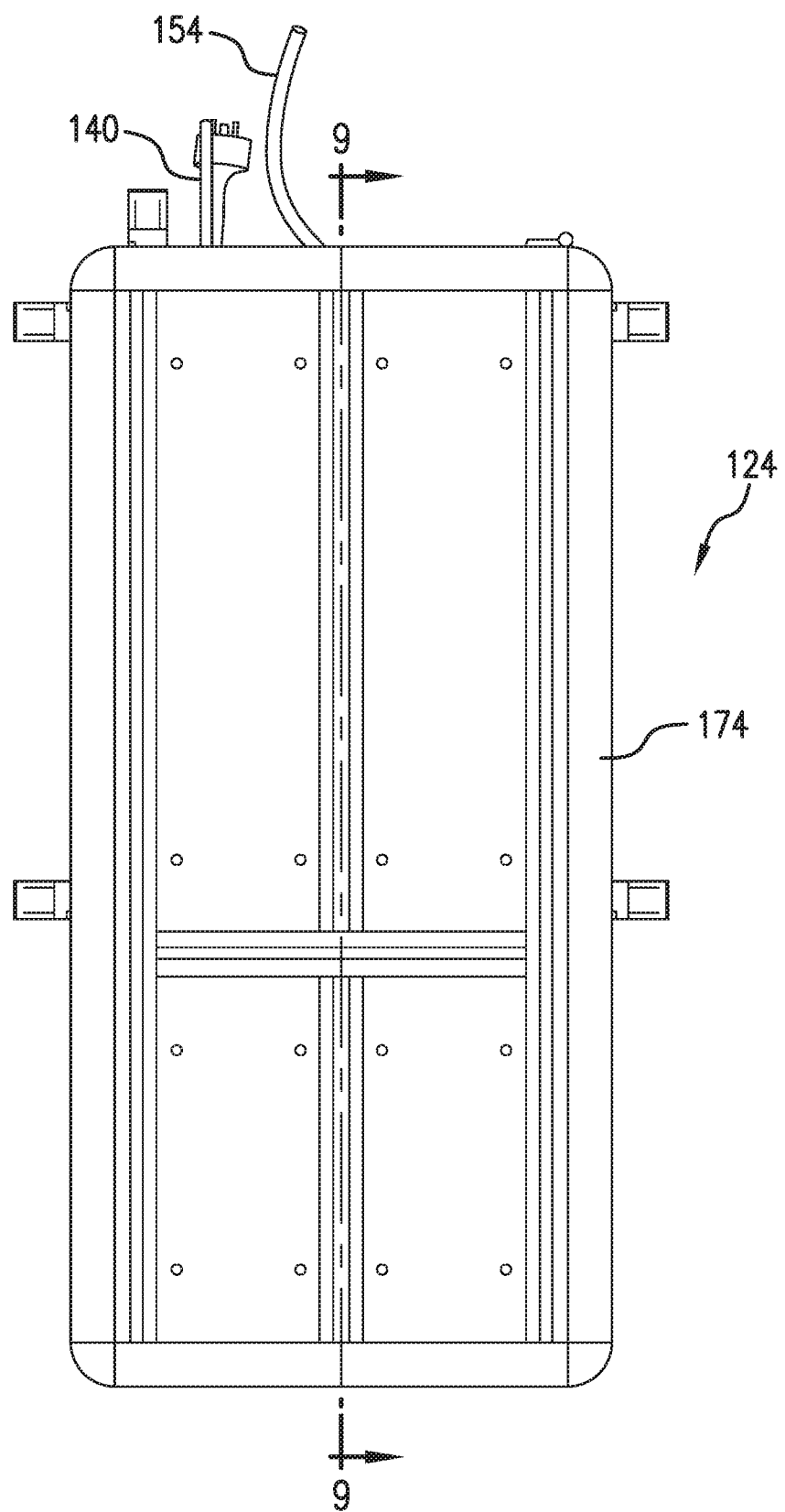
FIG. 9A is a top plan view of the dispensing apparatus of FIG. 9.
Figure 11:
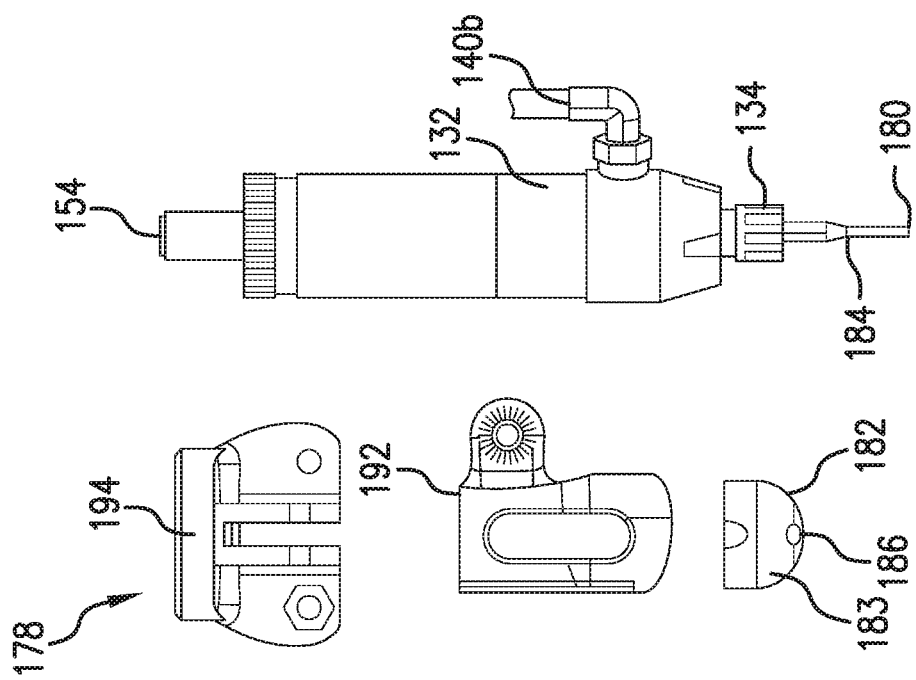
FIG. 11 is an assembly view of the elements of FIG. 10.
Figure 10:
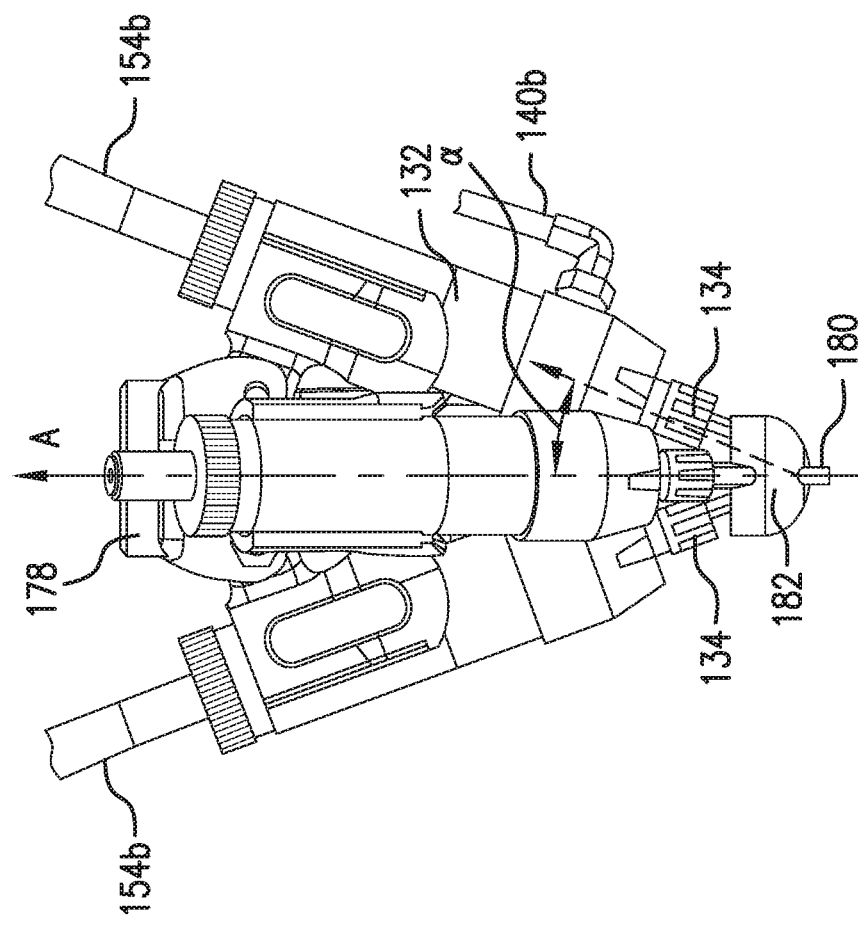
FIG. 10 is a front plan view of dispensers according to the embodiment of the system of FIG. 1.

Dispensers 132 are located within a preferred dispensing apparatus 124 as best shown in FIGS. 9 and 9A. FIG. 9A shows the top of a dispenser housing 174 which may be closed to keep out debris when in use in dispensing and when not in use. A typical instrumentation box having sliding or opening/closing panels with clear windows for operation may be used. The housing is configured with fittings to receive an entering compressed air conduit 154 from the pressure source 128 which also supplies the housing 152, but may be split or separate conduit run to provide compressed air from a common pressure source or the same pressure source 128 to the dispenser apparatus 124. The dispenser housing 174 preferably also accommodates an inlet for fluid delivery conduit 140 which may run for individual primary fluid components into the dispensing housing for delivery to nozzles 134 in the dispenser(s) 132. The same fluid conduit may be used if the lines are clear for alternating primary components to a split for each dispenser 132 or separate lines run from each container into the dispensing apparatus 124.

The compressed air conduit 154 is used to operate individual valves 130, shown here as solenoid valves, each of which is associated with a separate dispenser 132 and is configured to receive pressurized fluid, such as compressed air and/or pressurized fluid. The valves 130 are in preferred electronic communication with the controller or any associated microcontroller depending on the system design.

The dispenser(s) 132 each include individual nozzles 134, preferably one for each of the primary fluid components to be dispensed. As shown, four dispenser nozzles 134 are positioned in the dispenser apparatus 124 within the housing 174 and are held in place by a mounting apparatus 176 so that the nozzles are secure and located above a receptacle which will be placed in the dispensing apparatus 124 on the analytical scale 138 positioned within the housing 174. For a standard cosmetic bottle, the nozzle tips 180 should be above the neck of a standard cosmetic fill bottle. Each dispenser nozzle 134 has a metering valve 136 (such as a mini spool valve or a pinch valve) for metering fluid in predetermined quantities which are provided in the downloaded user-specific order information from the order management system. Each metering valve is connected to pressurized fluid component in communication with the pressurization source and to an individual solenoid valve 130 that pneumatically actuates the metering valve 136 allowing it to open and close. The solenoid valves are preferably three-way solenoid valves that may be independently actuated in response to a signal from the controller or associated microcontroller. Each metering valve 136 is also connected through fluid delivery conduit 140 to receive pressurized primary fluid components which are sent to the dispensers and to the valves from a bulk fluid which may be held in the fluid delivery apparatus as described above or in removable pressurized cartridges.

The dispenser nozzles 134 each have a nozzle tip 180 on a distal end 184 of the nozzle 134. To avoid contact between the tips, or the need to use specialty tips, and for stability, the dispensing apparatus 124 includes a nozzle tip holder 182 having a nozzle tip holder body 183. The nozzle tip holder is configured so as to define openings 186 extending longitudinally therethrough at inwardly directed angles and that are shaped and sized to receive the nozzle tips used. The openings 186 are angled and shaped so that when the nozzle tips 180 when passed through the nozzle tip hold extend downwardly from the holder and hold each nozzle so that each nozzle tip 180 is at an angle α with respect to the longitudinal axis A-A' running through the center of the mounting apparatus 178 and through the receptacle which is to be placed below the nozzle tip, but each nozzle tip is not in contact with any other nozzle tip. Preferably the nozzle tip(s) 180 are at an angle of about 45 to about 90 degrees, preferably about 60 to about 80 degrees, and more preferably about 70 to about 75 degrees with the longitudinal axis. Thus, the mounting apparatus 178 need not be moved or the nozzles to individually dispense different primary fluid components while keeping the receptacle in place during the dispensing process. Each nozzle holder may be pre-manufactured to specification depending on the nozzle size and design, or created using three dimensional printing for use, disposal and easy replacement.

The mounting apparatus 178 may be any suitable mounting apparatus. As shown, a pole 188 depends from an upper surface 190 of the dispenser housing 174. Each dispenser nozzle 132 is held by clamps 192 detachably connected to mounting bracket 194 which may be attached to the pole 188 through any suitable means.

The barcode scanner 118 used may be any suitable barcode scanner. It is preferred that the barcode scanner is easy to use, so that it may be a reader within a portable device, such as a cell phone with camera reader, a hand-held barcode reader, or a camera with barcode reading functionality. Preferably the barcode scanner is a quick read barcode scanner and in electronic communication with the controller or any associated microcontroller. The barcode scanner can be used at various positions in the system to load data, read instructions and the like. The barcode scanner should also be positioned and/or movable and have one or more of the software modules noted above (or its own separate software that is compatible with the system) so as to communicate with the controller and accept operator sign-in and identification information as well as user-specific instructions from the order management system.

In an alternative embodiment 300 as shown in FIG. 12, a fluid is dispensed in a fluid dispensing apparatus 324 having a removable cartridge 302 mounted in a frame 304 and receiving fluid in a series of incoming pressurized fluid conduits 306 in line with multiple fluid canisters 308 each for receiving a separate primary component. The bottom of each canister includes a canister nozzle 310 with a dispensing port 312. A source of pressure (which may be the same as the pressurization sources noted as suitable for the prior embodiment) and delivers pressurized air through lines 314 for opening and closing the canister nozzles. Each canister is in a cassette 316 that has data ports 318 for connecting to a mounted microcontroller 320. A receptacle is mounted on a holder 322 which is situated on an analytical balance 324, although other property measuring apparatus as noted above may be used for monitoring purposes. This alternative dispensing apparatus may be used with any of the other components as described herein.

The system 100 noted above may be employed in a method of preparing a customized cosmetic formulation. In the method, an order management system such as that noted above as order management system 104 is provided which has a server having user-specific data related to a custom cosmetic formulation and components thereof, wherein any of the data storage or database modules noted above with respect to the order management system and/or the controller may be used. A controller or controllers and/or associated microcontrollers is/are provided which are preferably configured to receive the data from the server. The controller(s) or microcontrollers if used are all preferably in communication with a graphical user interface, such as those noted above.

Data is sent from the server to the controller associated with an order for one or more custom cosmetic formulations as described herein. The order is received in the order management system and communicated to through the controller to the system herein. A pressure source is actuated to pressurize a fluid delivery apparatus, which may be any of the suitable pressure sources noted herein and/or the various embodiments of a fluid delivery apparatus. The fluid delivery apparatus is pressured so as to deliver one or more fluid components of a custom cosmetic formulation. One or more such orders may be processed in a batch. The fluid components are preferably delivered in order to one or more of a plurality of dispensers, each of which is associated with a fluid component of a custom cosmetic formulation in the order in a manner noted hereinabove. The controller actuates the pressure source and then the dispenser(s) as described herein are able to dispensing a fluid component from one of the plurality of dispensers into a receptacle suitable for receiving a custom cosmetic formulation. Dispensing occurs over a period of time associated with the property data received by the controller based on the component properties to provide the desired amount of a fluid components, e.g., weight may be monitored on a scale. The property, such as weight, of the component is monitored by a measuring device which measures a value associated with the property while dispensing, for example by using a balance or scale such as an analytical balance as noted above to measure weight as a property, which is preferably in electronic communication with the controller. A property value as monitored is compared to the desired property value for the fluid component to confirm that the amount of fluid component delivered is delivered to within a tolerance range for the predetermined property value of the fluid component, all of which data is stored in the order instructions downloaded by the controller from the order management system. When a tolerance value is reached, and the desired amount of the component is achieved, the dispensing is stopped for that fluid component as the measured property value is now at the predetermined property value and/or within the tolerance range for that property value. The final property value, such as weight, is recorded for authentication and compliance purposes after stopping the dispensing of the first fluid component. These dispensing steps are repeated for one or more additional primary fluid components in the order for the custom cosmetic formulation. The dispensed formulation is then mixed using any suitable mixer. Preferably a centrifuge, ball mill or other cosmetic mixer is used.

In the method, the controller may be or include one or more microcontrollers. The user-specific data may also comprise one or more of a user-specific component weight data for each cosmetic in the order for a custom cosmetic formulation, property data for each component in the order for a custom cosmetic formulation, and user-specific and/or operator-specific identification information as noted above.

The user-specific information received by the controller in the method, may be electronically communicated to a printer as described above and incorporated into a quick read barcode printed onto the receptacle or a label thereon prior to dispensing the fluid components in the order for a custom cosmetic formulation.

The operator identification data preferably includes log-in data so that an operator logs in through the graphical user interface which may be any of those noted above for receiving dispensing instructions and data associated with the order, and for confirming weight, and the status of the order at varying steps in the process, such as for confirming weight to authenticate the order and for compliance with cosmetic formulation requirements It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A system for preparing a custom cosmetic formulation, comprising:
    a controller in electronic communication with an order management system, wherein the order management system stores user-specific data including data related to a custom cosmetic formulation and components thereof;

a plurality of valves for receiving pressurized fluid, the plurality of valves in electronic communication with the controller;

a plurality of dispensers, each having a dispensing head having a nozzle, each nozzle comprising a metering valve for metering fluid in predetermined quantities and a nozzle tip on a distal end thereof, wherein the nozzle tips are arranged so as to dispense into an inlet of a product receptacle, a fluid introduced into the nozzle tip from the metering valve wherein the dispensers are in electronic communication with a data port and each of the metering valves is in communication with one of the plurality of valves for receiving pressurized fluid;

a measuring device in electronic communication with the controller, the measuring device capable of capturing data related to dispensed fluids from each of the plurality of dispensers and transmitting the data related to the dispensed fluids to the controller;

a barcode scanner for reading order-specific instructions;

a user interface for operator communication with the order management system and with the controller;

a plurality of fluid conduits for introducing fluid to the dispensers;

a fluid delivery apparatus for delivery of components of a custom cosmetic component to the dispensers; and a pressure source for pressurizing fluid in the fluid delivery apparatus for delivery of fluid from the fluid delivery apparatus to the plurality of dispensers.

2. The system according to claim 1, wherein the controller comprises at least one microcontroller.

3. The system according to claim 2, wherein the microcontroller is configured to receive data from the order management system, comprising
dispensing instructions;
one or more of user-specific component property data for each component of a custom cosmetic formulation; and
user-specific and/or operator-specific identification data.

4. The system according to claim 1, wherein the plurality of valves for receiving the pressurized fluid are solenoid valves.

5. The system according to claim 4, wherein there are four solenoid valves and each is a three-way solenoid valve, and wherein there are four dispensers.

6. The system according to claim 4, further comprising a relay shield in electronic communication with each of the plurality of solenoid valves and with the controller.

7. The system according to claim 4, wherein the pressure source is compressed air delivered through a series of compressed air conduits and the solenoid valves cycle compressed air to actuate the plurality of dispensers.

8. The system according to claim 7, wherein the solenoid valves actuate independently in response to a signal from the controller.

9. The system according to claim 7, wherein the dispensers are canister dispensers.

10. The system according to claim 9, wherein the canister dispensers arranged in a cassette, the cassette having a data port and being removable from the system.

11. The system according to claim 7, wherein the compressed air conduits are flexible tubing.

12. The system according to claim 1, wherein the barcode scanner is a camera having quick read barcode scanning functionality, and the barcode scanner is also capable of receiving operator sign-on and identification information.

13. The system according to claim 1, wherein the user interface is a graphical user interface.

14. The system according to claim 13, wherein the graphical user interface is a touchscreen.

15. The system according to claim 1, wherein the fluid conduits are flexible tubing.

16. The system according to claim 1, further comprising a nozzle tip holder, wherein the nozzle tip holder comprises a nozzle tip holder body defining openings longitudinally extending therethrough to hold each of the nozzle tips so that each tip is positioned to dispense over or within an opening into a neck of a receptacle having a longitudinal axis therethrough for receiving a dispensed fluid and each nozzle tip is at an angle with respect to the longitudinal axis of the receptacle, but each nozzle tip is not in contact with any other of the nozzle tips.

17. The system according to claim 1, wherein the data captured by the measuring device includes at least one of weight data, volumetric flow rate data, and viscosity data.

18. The system according to claim 1, wherein the measuring device is an analytical balance.

19. The system according to claim 18, wherein the analytical balance is capable of capturing and communicating to the controller weight data as fluid is metered through at least one nozzle tip.

20. The system according to claim 1, wherein the pressure source is compressed air delivered through a series of compressed air conduits and the compressed air conduits are positioned to introduce compressed air into the fluid delivery apparatus.

21. The system according to claim 1, wherein the fluid delivery apparatus comprises:
a first housing having an exterior surface and an interior surface defining an interior space, a removable lid, at least one pressure source inlet, and at least one fluid outlet;
at least one flexible fluid container arranged in the interior of the first housing, wherein the at least one flexible fluid container has a puncture seal cap and a puncture seal fitting for engaging the puncture seal cap;
a pressure controller for regulating pressure of a pressure source through the pressure source inlet;
at least one fluid delivery apparatus conduit having a first end in communication with the puncture seal fitting and a second end for delivery of fluid through the at least one fluid outlet to one of the fluid conduits in communication with the plurality of dispensers.

22. The system according to claim 21, wherein the flexible fluid container is positioned within an outer container.

23. The system according to claim 21, wherein there are two flexible fluid containers, each positioned within an outer container and the first housing has at least two fluid outlets, each of which is in communication with one of the fluid conduits leading to the plurality of dispensers.

24. The system according to claim 21, wherein the pressure source is compressed air delivered through compressed air conduits in fluid communication with the pressure source inlet.

25. The system according to claim 1, wherein the fluid delivery apparatus comprises
a plurality of housings, each of the plurality of housings having:
an exterior surface and an interior surface defining an interior space, a removable lid, at least one pressure source inlet, and at least one fluid outlet;
at least one flexible fluid container arranged in the interior of the first housing, wherein the at least one flexible fluid container has a puncture seal cap and a puncture seal fitting for engaging the puncture seal cap;

a pressure controller for regulating pressure of compressed air through the pressure source inlet;

at least one fluid delivery apparatus conduit having a first end in communication with the puncture seal fitting and a second end for delivery of fluid through the at least one fluid outlet to one of the fluid conduits in communication with the plurality of dispensers.

26. The system according to claim 25, wherein there are two flexible fluid containers in each of the housings, each of the two flexible fluid containers positioned within an outer container and the each of the housings having at least two fluid outlets, each of which fluid outlets is in communication with one of the fluid conduits leading to the plurality of dispensers.

27. The system according to claim 25, wherein the pressure source is compressed air delivered through compressed air conduits in fluid communication with the pressure source inlet.

28. The system according to claim 1, further comprising a mixing device, selected from a ball mill, a centrifuge, and a vibratory mixer.

29. The system according to claim 1, further comprising a printer in communication with the controller for provided printed user-specific information, based on data from the order management system, to a receptacle for housing a custom cosmetic formulation.

30. The system according to claim 29, wherein the printed user-specific information is printed on a label placed on a receptacle for housing a custom cosmetic formulation.

31. A system for preparing a custom cosmetic formulation, comprising:

a controller in electronic communication with an order management system, wherein the order management system stores user-specific data including data related to a custom cosmetic formulation and components thereof;

a plurality of valves for receiving pressurized fluid, the plurality of valves in electronic communication with the controller;

a plurality of dispensers, each having a dispensing head having a nozzle, and each nozzle comprising a metering valve for metering fluid in predetermined quantities and a nozzle tip on a distal end thereof, wherein the nozzle tips are arranged so as to dispense into an inlet of a product receptacle, a fluid introduced into the nozzle tip from the metering valve, wherein the dispensers are in electronic communication with a data port;

a nozzle tip holder comprising a nozzle tip holder body defining openings longitudinally extending therethrough to hold each of the nozzle tips so that each tip is positioned to dispense over or within an inlet of a product receptacle having a longitudinal axis therethrough for receiving a dispensed fluid and each nozzle tip is held at an angle with respect to the longitudinal axis of the receptacle, but each nozzle tip is not in contact with any other of the nozzle tips;

a measuring device in electronic communication with the controller, the measuring device capable of capturing data related to dispensed fluids from each of the plurality of dispensers and transmitting the data related to the dispensed fluids to the controller;

a barcode scanner for reading order-specific instructions;

a user interface for operator communication with the order management system and with the controller;

a plurality of fluid conduits for introducing fluid to the dispensers;

a fluid delivery apparatus for delivery of components of a custom cosmetic component to the dispensers; and a pressure source for pressurizing fluid in the fluid delivery apparatus for delivery of fluid from the fluid delivery apparatus to the plurality of dispensers.

32. The system according to claim 31, wherein the nozzle holder is printed through three-dimensional printing to accommodate the nozzle tips and so that the nozzle holder is disposable and replaceable.

33. The system according to claim 31, wherein each metering valve is selected from a mini-spool valve and a pinch valve.

34. The system according to claim 1, wherein each metering valve is selected from a mini-spool valve and a pinch valve.

35. The system according to claim 16, wherein the nozzle holder is printed through three-dimensional printing to accommodate the nozzle tips and so that the nozzle holder is disposable and replaceable.

* * * * *